US009447433B2

(12) United States Patent
Hirsch et al.

(10) Patent No.: US 9,447,433 B2
(45) Date of Patent: Sep. 20, 2016

(54) SYNTHETIC ADENO-ASSOCIATED VIRUS INVERTED TERMINAL REPEATS

(71) Applicant: The University of North Carolina at Chapel Hill, Chapel Hill, NC (US)

(72) Inventors: Matthew Louis Hirsch, Chapel Hill, NC (US); Richard Jude Samulski, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/211,927

(22) Filed: Mar. 14, 2014

(65) Prior Publication Data

US 2014/0271551 A1    Sep. 18, 2014

Related U.S. Application Data

(60) Provisional application No. 61/787,374, filed on Mar. 15, 2013.

(51) Int. Cl.
*C12N 15/86* (2006.01)

(52) U.S. Cl.
CPC ..... *C12N 15/86* (2013.01); *C12N 2750/14141* (2013.01)

(58) Field of Classification Search
CPC ....................................................... C12N 15/86
USPC .................................. 435/235.1, 320.1, 456
See application file for complete search history.

(56) References Cited

U.S. PATENT DOCUMENTS

2013/0109742 A1* 5/2013 Hewitt et al. ............... 514/44 R

OTHER PUBLICATIONS

Young et al. PNAS, Nov. 20, 2001_vol. 98_No. 24_13525-13530.*
Krieg et al. Proc. Natl. Acad. Sci. USA, vol. 95, pp. 12631-12636, Oct. 1998.*
Grimm et al., "Liver Transduction with Recombinant Adeno-Associated Virus Is Primarily Restricted by Capsid Serotype Not Vector Genotype", *Journal of Virology*, 2006, 80(1): 426-439.
Hewitt et al., "Creating a novel origin of replication through modulating DNA-protein interfaces" *PLoS One*, 2010, 5(1): p. e8850.
McCarty et al., "Self-complementary recombinant adeno-associated virus (scAAV) vectors promote efficient transduction independently of DNA synthesis", *Gene Therapy*, 2001, 8: 1248-1254.
Xiao et al., "A Novel 165-Base-Pair Terminal Repeat Sequence Is the Sole *cis* Requirement for the Adeno-Associated Virus Life Cycle", *Journal of Virology*, 1997, 71(2): 941-948.
Zhong et al., "Single-polarity Recombinant Adeno-associated Virus 2 Vector-mediated Transgene Expression In Vitro and In Vivo: Mechanism of Transduction", *Molecular Therapy*, 2008, 16(2): 290-295.
Daya et al. "Gene Therapy Using Adeno-Associated Virus Vectors", *Clinical Microbiology Reviews* 21(4):583-593 (2008).
Hatfield et al. "The NFIII/OCT-1 Binding Site Stimulates Adenovirus DNA Replication In Vivo and is Functionally Redundant with Adjacent Sequences", *J. Virology* 67(7):3931-3939 (1993).
Krieg et al. "Sequence motifs in adenoviral DNA block immune activation by stimulatory CpG motifs", *Proc. Natl. Acad. Sci. USA* 95:12631-12636 (1998).
Mays et al. "Adeno-Associated Virus Capsid Structure Drives CD4-Dependent $CD8^+$ T Cell Response to Vector Encoded Proteins", *J. Immunology* 182:6051-6060 (2009).
Song et al. "Effect of DNA-dependent protein kinase on the molecular fate of the rAAV2 genome in skeletal muscle", *PNAS* 98(7):4084-4088 (2001).
Yan et al. "Inverted Terminal Repeat Sequences are Important for Intermolecular Recombination and Circularization of Adeno-Associated Virus Genomes", *J. Virology* 79(1):364-379 (2005).
Young et al. "Roles of Adeno-Associated Virus Rep Protein and Human Chromosome 19 in Site-Specific Recombination", *J. Virology* 74(9):3953-3966 (2000).
Young et al. "Adeno-associated virus (AAV) site-specific recombination does not require a Rep-dependent origin of replication within the AAV terminal repeat", *PNAS* 98(24):13525-13530 (2001).
Notification of Transmittal of International Search Report and the Written Opinion of the International Search Authority, or the Declaration corresponding to PCT Application No. PCT/US2014/028119 mailed Jul. 16, 2014.
International Preliminary Report on Patentability corresponding to International Patent Application No. PCT/US2014/028119 (6 pages) (dated Sep. 15, 2015).

* cited by examiner

*Primary Examiner* — Janet Epps-Smith
(74) *Attorney, Agent, or Firm* — Myers Bigel & Sibley, P.A.

(57) ABSTRACT

This invention relates to synthetic adeno-associated virus (AAV) inverted terminal repeats (ITRs) that exhibit altered activities compared to a naturally occurring AAV ITR and methods of using the same for delivery of nucleic acids to a cell or a subject. The synthetic ITRs provide a larger packaging capacity and the ability to manipulate activities such as transduction efficiency, cellular response to transduction, and transcription.

18 Claims, 12 Drawing Sheets

| FACTOR | AAV ITR2 | ITR-257 | ITR-258 |
|---|---|---|---|
| p53 | 6 | 1 | 1 |
| NFI/CTF | 1 | 0 | 0 |
| SRY | 1 | 0 | 0 |
| PAX5 | 4 | 1 | 1 |
| TCF-4E | 2 | 1 | 1 |
| GR-α | 2 | 1 | 1 |
| SP1 | 1 | 0 | 0 |
| C/EBPβ | 2 | 1 | 1 |
| LEF-1 | 2 | 1 | 1 |

*FIG. 3*

| INVERTED REPEAT | NUCLEOTIDES | PREDICTED SHAPE | CpGs | rAAV2 TITER (vg/µl) |
|---|---|---|---|---|
| AAV2 | 165 | | 16 | 4.4e8 |
| MH257 | 167 | | 8 | 9.1e8 |
| MH258 | 143 | | 8 | 2.1e8 |
| MH261 | 113 | | 8 | NO rAAV |

FIG. 5

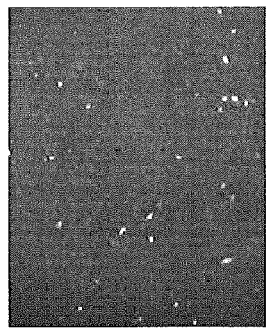
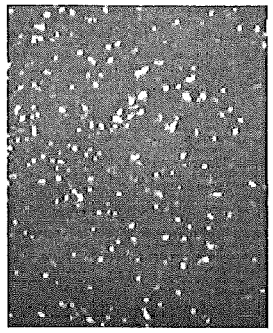
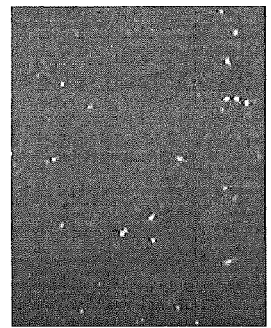
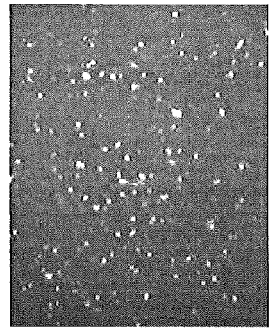
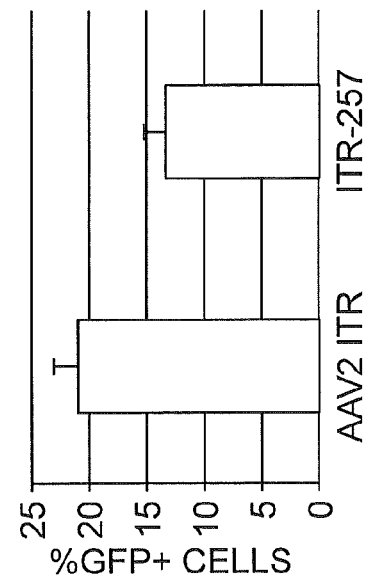
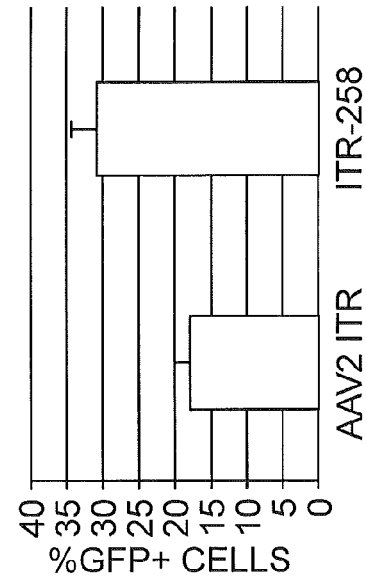
FIG. 7A
FIG. 7B
FIG. 7C
FIG. 7D

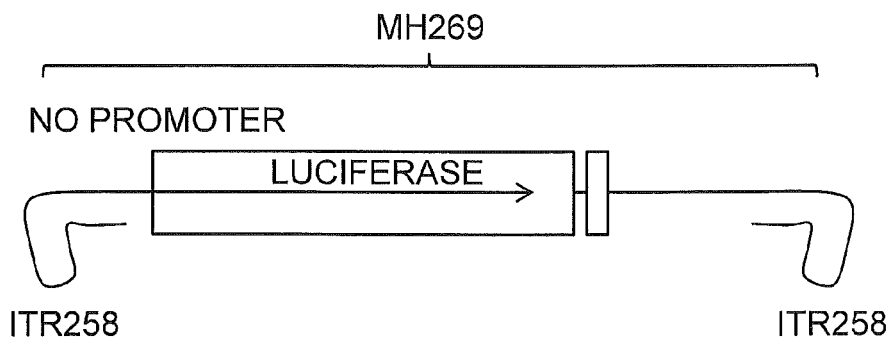
*FIG. 12*

SEQUENCE LISTING

```
<160> NUMBER OF SEQ ID NOS: 17

<210> SEQ ID NO 1
<211> LENGTH: 167
<212> TYPE: DNA
<213> ORGANISM: Artificial
<220> FEATURE:
<223> OTHER INFORMATION: Synthetic AAV ITR sequence

<400> SEQUENCE: 1
aggaacccct agtgatggag ttggccactc cctctctgcg cgctcgctcg ctcactgagg      60
caatttgata aaaatcgtca aattataaac aggctttgcc tgtttagcct cagtgagcga    120
gcgagcgcgc agagagggag tggccaactc catcactagg ggttcct                  167

<210> SEQ ID NO 2
<211> LENGTH: 143
<212> TYPE: DNA
<213> ORGANISM: Artificial
<220> FEATURE:
<223> OTHER INFORMATION: Synthetic AAV ITR sequence

<400> SEQUENCE: 2
aggaacccct agtgatggag ttggccactc cctctctgcg cgctcgctcg ctcactgagg      60
gataaaaatc aggctttgc ctgcctcagt gagcgagcga gcgcgcagag agggagtggc     120
caactccatc actaggggtt cct                                            143

<210> SEQ ID NO 3
<211> LENGTH: 143
<212> TYPE: DNA
```

<213> ORGANISM: Artificial
<220> FEATURE:
<223> OTHER INFORMATION: Synthetic AAV ITR sequence

<400> SEQUENCE: 3

```
aggaacccct agtgatggag ttggccactc cctctctgcg cgctcgctcg ctcactgagg    60
gataaaaatc caggctttgc ctgcctcagt gagcgagcga gcgcgcagag agggagtggc   120
caactccatc actagggggtt cct                                          143
```

<210> SEQ ID NO 4
<211> LENGTH: 208
<212> TYPE: DNA
<213> ORGANISM: Artificial
<220> FEATURE:
<223> OTHER INFORMATION: Synthetic AAV ITR sequence

<400> SEQUENCE: 4

```
aggaacccct agtgatggag ttggccactc cctctctggg attgggattg cgcgctcgct    60
cgcgggattg ggattgggat tgggattggg attggggattg ataaaaatca atcccaatcc  120
caatcccaat cccaatccca atcccgcgag cgagcgcgca atcccaatcc cagagaggga  180
gtggccaact ccatcactag gggttcct                                      208
```

<210> SEQ ID NO 5
<211> LENGTH: 199
<212> TYPE: DNA
<213> ORGANISM: Artificial
<220> FEATURE:
<223> OTHER INFORMATION: Synthetic AAV ITR sequence

<400> SEQUENCE: 5

```
aggaacccct agtgatggag ttggccactc cctctctgcg cgctcgctcg ctcgggattg    60
ggattgggat tgggattggg attggggattg ataaaaatca atcccaatcc caatcccaat  120
cccaatccca atcccgcgag cgagcgcgca ggagagggag tggccaactc catcactagg  180
ggttcctaag cttattata                                                199
```

<210> SEQ ID NO 6
<211> LENGTH: 154
<212> TYPE: DNA
<213> ORGANISM: Artificial
<220> FEATURE:
<223> OTHER INFORMATION: Synthetic AAV ITR sequence

<400> SEQUENCE: 6

```
aggaacccct agtgatggag ttggccactc cctctctgcg cgctcgctcg ctcactgagg    60
gcgcctataa agataaaaat ccaggctttg cctgcctcag ttagcgagcg agcgcgcaga  120
gagggagtgg ccaactccat cactagggggt tcct                              154
```

<210> SEQ ID NO 7
<211> LENGTH: 127
<212> TYPE: DNA
<213> ORGANISM: Artificial
<220> FEATURE:
<223> OTHER INFORMATION: Synthetic AAV ITR sequence

<400> SEQUENCE: 7

```
ctagtgatgg agttggccac tccctctctg cgcgctcgct cgctcactga gggataaaaa    60
tccaggcttt gcctgcctca gtgagcgagc gagcgcgcag agagggagtg gccaactcca  120
tcactag                                                            127
```

<210> SEQ ID NO 8
<211> LENGTH: 165
<212> TYPE: DNA
<213> ORGANISM: adeno-associated virus 2

<400> SEQUENCE: 8
aggaacccct agtgatggag ttggccactc cctctctgcg cgctcgctcg ctcactgagg      60
ccgggcgacc aaaggtcgcc cgacgcccgg gctttgcccg gcggcctca gtgagcgagc      120 gagcgcgcag agagggagtg gccaactcca tcactagggg ttcct                     165

<210> SEQ ID NO 9
<211> LENGTH: 143
<212> TYPE: DNA
<213> ORGANISM: adeno-associated virus 2

<400> SEQUENCE: 9
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg      120
gccaactcca tcactagggg ttc                                             143

<210> SEQ ID NO 10
<211> LENGTH: 49
<212> TYPE: DNA
<213> ORGANISM: adeno-associated virus 2

<400> SEQUENCE: 10
ggccgggcga ccaaaggtcg cccgacgccc gggctttgcc cgggcggcc                  49

<210> SEQ ID NO 11
<211> LENGTH: 53
<212> TYPE: DNA
<213> ORGANISM: Artificial
<220> FEATURE:
<223> OTHER INFORMATION: Synthetic AAV ITR sequence

<400> SEQUENCE: 11
aggcaatttg ataaaaatcg tcaaattata acaggcttt gcctgtttag cct              53

<210> SEQ ID NO 12
<211> LENGTH: 33
<212> TYPE: DNA
<213> ORGANISM: Artificial
<220> FEATURE:
<223> OTHER INFORMATION: Synthetic AAV ITR sequence

<400> SEQUENCE: 12
tgagggataa aaatccaggc tttgcctgcc tca                                   33

<210> SEQ ID NO 13
<211> LENGTH: 16
<212> TYPE: DNA
<213> ORGANISM: Artificial
<220> FEATURE:
<223> OTHER INFORMATION: Synthetic AAV ITR sequence

<400> SEQUENCE: 13
cgcgataaaa atcgcg                                                      16

<210> SEQ ID NO 14
<211> LENGTH: 122
<212> TYPE: DNA

```
<213> ORGANISM: adeno-associated virus 2

<400> SEQUENCE: 14
gccactccct ctctgcgcgc tcgctcgctc actgaggccg ggcgaccaaa ggtcgcccga      60
cgcccgggct tgcccgggc ggcctcagtg agcgagcgag cgcgcagaga gggagtggcc     120
aa                                                                   122

<210> SEQ ID NO 15
<211> LENGTH: 124
<212> TYPE: DNA
<213> ORGANISM: Artificial
<220> FEATURE:
<223> OTHER INFORMATION: Synthetic AAV ITR sequence

<400> SEQUENCE: 15
gccactccct ctctgcgcgc tcgctcgctc actgaggcaa tttgataaaa atcgtcaaat     60
tataaacagg ctttgcctgt ttagcctcag tgagcgagcg agcgcgcaga gagggagtgg    120
ccaa                                                                 124

<210> SEQ ID NO 16
<211> LENGTH: 100
<212> TYPE: DNA
<213> ORGANISM: Artificial
<220> FEATURE:
<223> OTHER INFORMATION: Synthetic AAV ITR sequence

<400> SEQUENCE: 16
gccactccct ctctgcgcgc tcgctcgctc actgagggat aaaaatccag gctttgcctg     60
cctcagtgag cgagcgagcg cgcagagagg gagtggccaa                          100

<210> SEQ ID NO 17
<211> LENGTH: 69
<212> TYPE: DNA
<213> ORGANISM: Artificial
<220> FEATURE:
<223> OTHER INFORMATION: Synthetic AAV ITR sequence

<400> SEQUENCE: 17
gccactccct ctctgcgcgc tcgctcgcga taaaaatcgc gagcgagcgc gcagagaggg     60
agtggccaa                                                             69
```

SYNTHETIC ADENO-ASSOCIATED VIRUS INVERTED TERMINAL REPEATS

STATEMENT OF PRIORITY

The present invention claims the benefit, under 35 U.S.C. §119(e), of U.S. Provisional Application No. 61/787,374, filed Mar. 15, 2013, the entire contents of which are incorporated by reference herein.

STATEMENT REGARDING ELECTRONIC FILING OF A SEQUENCE LISTING

A Sequence Listing in ASCII text format, submitted under 37 C.F.R. §1.821, entitled 5470-663TS_ST25.txt, 5,465 bytes in size, generated on Jun. 3, 2014 and filed via EFS-Web, is provided in lieu of a paper copy. This Sequence Listing is incorporated by reference into the specification for its disclosures.

FIELD OF THE INVENTION

This invention relates to synthetic adeno-associated virus (AAV) inverted terminal repeats (ITRs) that exhibit altered activities compared to a naturally occurring AAV ITR and methods of using the same for delivery of nucleic acids to a cell or a subject. The synthetic ITRs can provide a larger packaging capacity and the ability to manipulate activities such as transduction efficiency, cellular response to transduction, and transcription.

BACKGROUND OF THE INVENTION

AAV is a small (25 nm) single-strand DNA virus that is ubiquitous in nature. Initial characterizations of this virus demonstrated that it is non-autonomous since replication and production relies on helper functions provided by other viruses including adenovirus (hence its name) [1]. AAV is a simple virus composed only of a non-enveloped protein capsid and a single-strand DNA molecule that is flanked at each end by T-shaped ITRs. The AAV ITRs provide necessary functions for AAV production and transduction including acting as the viral origin, capsid packaging, second-strand synthesis in the host cell, and genome persistence [1]. Regarding the viral capsid, many serotypes have been identified that alter cell tropism due to the use of different cellular receptors [2].

The first AAV vector was generated over 30 years ago by the demonstration that the ITRs of AAV serotype 2 (ITR2) confer the abilities of plasmid replication and single-strand DNA capsid packaging in the presence of the AAV replication and capsid genes, along with the required adenovirus helper functions [3, 4]. This seminal observation resulted in the ability to produce AAV transgenic DNA vectors in which the only viral DNA sequence are the ITRs, with a remaining 4.5 kb sequence of choice [1]. Since that initial report, AAV vectors are now among the most promising methods of gene delivery for the treatment of human genetic diseases. To date, over 80 clinical trials using AAV vectorology have been performed and all have utilized the ITR2 sequence necessary for transgenic DNA replication, packaging, second-strand synthesis and persistence [1].

Due to the technical difficulties of ITR synthesis, only a few reports in the last 32 years have demonstrated the ability to synthesize functional mutant ITR2 sequences capable of AAV vector production and transduction [5-8]. In all of these cases, the generated ITR sequences were based on the natural ITR isolate from AAV serotype 2 and, in a single recent report, hybrid ITRs using the natural ITR sequence of AAV serotype 5 [5]. An additional study compared the wild type ITRs of AAV serotypes 1-6 at the levels of production and in vivo transduction [10]. The collective conclusion of that work was that the natural ITRs (1-6) did not significantly affect vector production or the transduction efficiency in mouse liver [10].

The present invention provides alternatives to ITR2 that have improved characteristics and are suitable for generating vectors with a wide variety of uses, including gene therapy.

SUMMARY OF THE INVENTION

The present invention relates to the development of synthetic AAV ITRs that have desirable characteristics and can be designed to manipulate the activities of and cellular responses to vectors comprising the ITRs.

One aspect of the invention relates to a polynucleotide comprising at least one synthetic AAV ITR, wherein said ITR comprises: (a) an AAV rep binding element; (b) an AAV terminal resolution sequence; and (c) an AAV RBE' element; wherein said ITR does not comprise any other AAV ITR sequences. The invention further relates to a viral vector and a recombinant AAV particle comprising the polynucleotide of the invention. Further provided are pharmaceutical formulations comprising a virus particle of the invention in a pharmaceutically acceptable carrier.

An additional aspect of the invention relates to a polynucleotide comprising at least one synthetic AAV ITR, wherein the nucleotide sequence of one or more transcription factor binding sites in said ITR is deleted and/or substituted, relative to the sequence of a naturally occurring AAV ITR such as ITR2.

A further aspect of the invention relates to a polynucleotide comprising at least one synthetic AAV ITR, wherein one or more CpG motifs in said ITR are deleted and/or substituted, relative to the sequence of a naturally occurring AAV ITR such as ITR2.

In some embodiments, the synthetic ITR does not induce apoptosis in a host cell, e.g., in stem cells or cancer cells, as ITR2 has been reported to do.

In some embodiments, the ITR elicits altered p53 activation when transduced into a host cell.

In some embodiments, the synthetic ITR elicits altered cell cycle progression when transduced into a host cell.

In some embodiments, the synthetic ITR elicits altered DNA damage response when transduced into a host cell.

In certain embodiments, the synthetic ITR is enhanced for intra- or inter-molecular homologous recombination.

In certain embodiments, the synthetic ITR exhibits increased host chromosome integration of transduced vector genomes. In other embodiments, the ITR exhibits decreased host chromosome integration of transduced vector genomes.

An additional aspect of the invention relates to a method of producing a recombinant AAV particle, comprising providing to a cell permissive for AAV replication: (a) a recombinant AAV template comprising (i) a heterologous nucleotide sequence, and (ii) the synthetic ITR of the invention; (b) a polynucleotide comprising Rep coding sequences and Cap coding sequences; under conditions sufficient for the replication and packaging of the recombinant AAV template; whereby recombinant AAV particles are produced in the cell.

A further aspect of the invention relates to a method of delivering a nucleic acid to a cell, comprising introducing into a cell the recombinant AAV particle of the invention.

Another aspect of the invention relates to a method of administering a nucleic acid to a mammalian subject comprising administering to the mammalian subject a cell that has been contacted with the recombinant AAV particle of the invention under conditions sufficient for the AAV particle vector genome to enter the cell.

A further aspect of the invention relates to a method of administering a nucleic acid to a mammalian subject comprising administering to the mammalian subject the recombinant AAV particle of the invention.

Another aspect of the invention relates to a method of increasing the transgenic DNA packaging capacity of an AAV vector, comprising generating a vector comprising at least one synthetic AAV ITR, wherein said ITR comprises: (a) an AAV rep binding element; (b) an AAV terminal resolution sequence; and (c) an AAV RBE' element; wherein said ITR does not comprise any other AAV ITR sequences.

An additional aspect of the invention relates to a method of altering the cellular response to infection by an AAV vector, comprising generating a vector comprising at least one synthetic ITR, wherein the nucleotide sequence of one or more transcription factor binding sites in said ITR is deleted and/or substituted, relative to the sequence of a naturally occurring AAV ITR such as ITR2, wherein the vector comprising at least one synthetic ITR produces an altered cellular response to infection.

A further aspect of the invention relates to a method of altering the cellular response to infection by an AAV vector, comprising generating a vector comprising at least one synthetic ITR, wherein one or more CpG motifs in said ITR are deleted and/or substituted, relative to the sequence of a naturally occurring AAV ITR such as ITR2, wherein the vector comprising at least one synthetic ITR produces an altered cellular response to infection.

Another aspect of the invention relates to use of the recombinant AAV particle of the invention for delivering a nucleic acid to a cell.

An additional aspect of the invention relates to use of a cell that has been contacted with the recombinant AAV particle of the invention for delivering a nucleic acid to a mammalian subject.

A further aspect of the invention relates to use of the recombinant AAV particle of the invention for delivering a nucleic acid to a mammalian subject.

Another aspect of the invention relates to use of the recombinant AAV particle of the invention for the manufacture of a medicament for delivering a nucleic acid to a cell.

An additional aspect of the invention relates to use of a cell that has been contacted with the recombinant AAV particle of the invention for the manufacture of a medicament for delivering a nucleic acid to a mammalian subject.

A further aspect of the invention relates to use of the recombinant AAV particle of the invention for the manufacture of a medicament for delivering a nucleic acid to a mammalian subject.

These and other aspects of the invention are set forth in more detail in the description of the invention below.

BRIEF DESCRIPTION OF THE DRAWINGS

FIG. 3 shows the AGGEN analysis of putative transcription factor binding sites in synthetic ITRs.

FIG. 5 shows synthetic ITR sequences and attributes (SEQ ID NOS:10-13 and 14-17).

FIG. 6 shows a sequence alignment of synthetic ITR sequences (SEQ ID NOS:14-17).

FIGS. 7A-7D show synthetic ITR transduction in vitro. The indicated ITR was used for transduction of the indicated cell type (using a CMV-eGFP cassette).

FIG. 12 shows synthetic ITR-258 functions as a promoter in vivo. The depicted construct was packaged in AAV8 and administered to WT mice via the IV route. Three weeks later mice were imaged for luciferase activity.

DETAILED DESCRIPTION OF THE INVENTION

Figure 1:
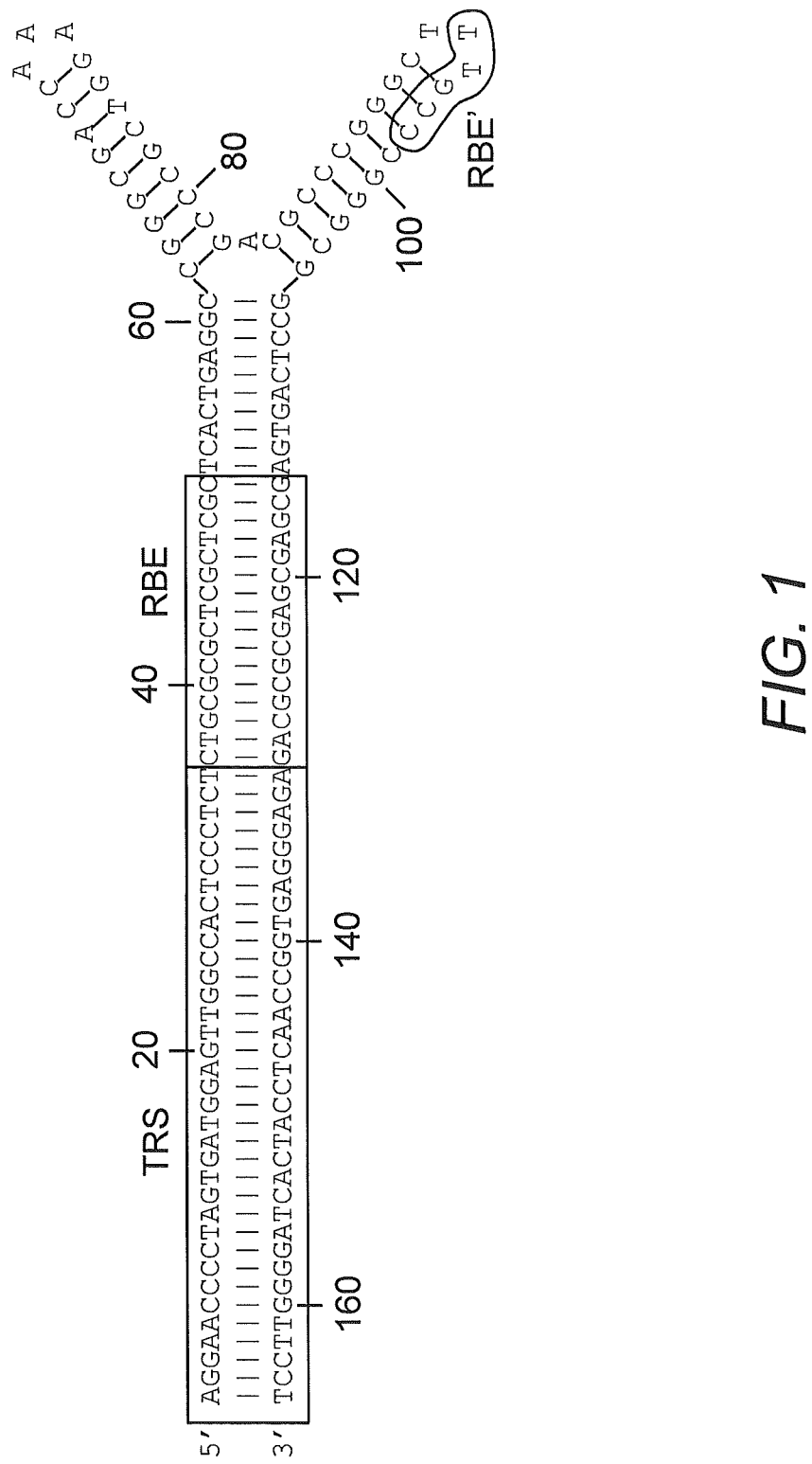
FIG. 1 shows a map of the elements in the AAV2 ITR (SEQ ID NO:8).

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR §1.822 and established usage. See, e.g., *PatentIn User Manual*, 99-102 (November 1990) (U.S. Patent and Trademark Office).

Except as otherwise indicated, standard methods known to those skilled in the art may be used for the construction of recombinant AAV (rAAV) constructs, packaging vectors expressing the AAV Rep and/or Cap sequences, and transiently and stably transfected packaging cells. Such techniques are known to those skilled in the art. See, e.g., SAMBROOK et al. MOLECULAR CLONING: A LABORATORY MANUAL 2nd Ed. (Cold Spring Harbor, N.Y., 1989); AUSUBEL et al. CURRENT PROTOCOLS IN MOLECULAR BIOLOGY (Green Publishing Associates, Inc. and John Wiley & Sons, Inc., New York).

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

DEFINITIONS

The following terms are used in the description herein and the appended claims.

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 20%, 10%, 5%, 1%, 0.5%, or even 0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" is to be interpreted as encompassing the recited materials or steps "and those that do not materially affect the basic and novel characteristic(s)" of the claimed invention (e.g., rAAV replication). See, In re Herz, 537 F.2d 549, 551-52, 190 U.S.P.Q. 461, 463 (CCPA 1976) (emphasis in the original); see also MPEP §2111.03. Thus, the term "consisting essentially of" as used herein should not be interpreted as equivalent to "comprising."

The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al. VIROLOGY, volume 2, chapter 69 (4th ed., Lippincott-Raven Publishers).

The genus Dependovirus contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIELDS et al. VIROLOGY, volume 2, chapter 69 (4th ed., Lippincott-Raven Publishers); and Table 1.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any other AAV now known or later discovered. See, e.g., FIELDS et al. VIROLOGY, volume 2, chapter 69 (4th ed., Lippincott-Raven Publishers). A number of relatively new AAV serotypes and clades have been identified (See, e.g., Gao et al. (2004) J. Virol. 78:6381; Moris et al. (2004) Virol. 33-:375; and Table 1).

The AAV particles and genomes of the present invention can be from any AAV. The genomic sequences of various serotypes of AAV, as well as the sequences of the native ITRs, Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching AAV nucleic acid and amino acid sequences. See also, e.g., Bantel-Schaal et al. (1999) J. Virol. 73: 939; Chiorini et al. (1997) J. Virol. 71:6823; Chiorini et al. (1999) J. Virol. 73:1309; Gao et al. (2002) Proc. Nat. Acad. Sci. USA 99:11854; Moris et al. (2004) Virol. 33-:375-383; Mori et al. (2004) Virol. 330:375; Muramatsu et al, (1996) Virol, 221:208; Ruffing et al. (1994) J. Gen. Virol. 75:3385; Rutledge et al. (1998)J. Virol. 72:309; Schmidt et al. (2008) J. Virol. 82:8911; Shade et al., (1986) J. Virol. 58:921; Srivastava et al. (1983) J. Virol, 45:555; Xiao et al. (1999) J. Virol. 73:3994; international patent publications WO 00/28061, WO 99/61601, WO 98/11244; and U.S. Pat. No. 6,156,303; the disclosures of which are incorporated by reference herein for teaching AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, Pa. (incorporated herein it its entirety).

The term "tropism" as used herein refers to entry of the virus into the cell, optionally and preferably followed by expression (e.g., transcription and, optionally, translation) of sequences carried by the viral genome in the cell, e.g., for a recombinant virus, expression of the heterologous nucleotide sequences(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of AAV, gene expression from the viral genome may be from a stably integrated provirus, from a non-integrated episome, as well as any other form in which the virus may take within the cell.

As used herein, "transduction" of a cell by AAV refers to AAV-mediated transfer of genetic material into the cell. See, e.g., FIELDS et al. VIROLOGY, volume 2, chapter 69 (3d ed., Lippincott-Raven Publishers).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

TABLE 1

| Complete Genomes | GenBank Accession Number |
| --- | --- |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |

TABLE 1-continued

| Complete Genomes | GenBank Accession Number |
| --- | --- |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |

TABLE 1-continued

| Complete Genomes | GenBank Accession Number |
| --- | --- |
| Rh33 | AY243002 |
| Rh32 | AY243003 |

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), and can be either single or double stranded DNA sequences.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351 (1987); the method is similar to that described by Higgins & Sharp, CABIOS 5:151 (1989).

Another example of a useful algorithm is the BLAST algorithm, described in Altschul et al., J. Mol. Biol. 215:403 (1990) and Karlin et al., Proc. Natl. Acad. Sci. USA 90:5873 (1993). A particularly useful BLAST program is the WU-BLAST-2 program which was obtained from Altschul et al., Meth. Enzymol., 266:460 (1996); blast.wustl/edu/blast/RE-ADME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., Nucleic Acids Res. 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components or other polypeptides or nucleic acids commonly found associated with the polynucleotide.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

By the terms "treat," "treating," or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. In some embodiments, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone or a plasmid.

The virus vectors of the invention can further be duplexed AAV particles as described in international patent publication WO 01/92551 (the disclosure of which is incorporated herein by reference in its entirety). Thus, in some embodiments, double stranded (duplex) genomes can be packaged.

A "rAAV vector genome" or "rAAV genome" is an AAV genome (i.e., vDNA) that comprises one or more heterologous nucleic acid sequences. rAAV vectors generally require only the 145 base ITR in cis to generate virus. Typically, the rAAV vector genome will only retain the one or more ITR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one ITR sequence (e.g., AAV ITR sequence), optionally two ITRs (e.g., two AAV ITRs), which typically will be at the 5' and 3' ends of the vector genome and flank the heterologous nucleic acid, but need not be contiguous thereto. The ITRs can be the same or different from each other.

An "AAV inverted terminal repeat" or "AAV ITR" may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered (see, e.g., Table 1). An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, persistence, and/or provirus rescue, and the like.

The virus vectors of the invention can further be "targeted" virus vectors (e.g., having a directed tropism) and/or a "hybrid" AAV (i.e., in which the viral ITRs and viral capsid are from different AAV) as described in international patent publication WO 00/28004 and Chao et al., (2000) *Mol. Therapy* 2:619.

Further, the viral capsid or genomic elements can contain other modifications, including insertions, deletions and/or substitutions.

The term "template" or "substrate" is used herein to refer to a polynucleotide sequence that may be replicated to produce the AAV viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, AAV "Rep coding sequences" indicate the nucleic acid sequences that encode the AAV non-structural proteins that mediate viral replication and the production of new virus particles, The AAV replication genes and proteins have been described in, e.g., FIELDS et al. VIROLOGY, volume 2, chapters 69 & 70 (4th ed., Lippincott-Raven Publishers).

The "Rep coding sequences" need not encode all of the AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) *Human Gene Therapy* 13:1935).

As used herein, the AAV "cap coding sequences" encode the structural proteins that form a functional AAV capsid (i.e., can package DNA and infect target cells). Typically, the cap coding sequences will encode all of the AAV capsid subunits, but less than all of the capsid subunits may be encoded as long as a functional capsid is produced. Typically, but not necessarily, the cap coding sequences will be present on a single nucleic acid molecule.

The capsid structure of AAV are described in more detail in BERNARD N. FIELDS et al., VIROLOGY, volume 2, chapters 69 & 70 (4th ed., Lippincott-Raven Publishers).

As used herein, the term "synthetic AAV ITR" refers to a non-naturally occurring ITR that differs in nucleotide sequence from the AAV serotype 2 ITR (ITR2) sequence due to one or more deletions, additions, substitutions, or any combination thereof. The difference between the synthetic and ITR2 sequences may be as little as a single nucleotide change, e.g., a change in 1, 2, 3, 4, 5, 6, 7, 8, 9, 10, 15, 20, 25, 30, 35, 40, 45, 60, 60, 70, 80, 90, or 100 or more nucleotides or any range therein.

Synthetic AAV ITRs

The present invention provides synthetic AAV ITRs that have desirable characteristics and can be designed to manipulate the activities of and cellular responses to vectors comprising the ITRs.

One aspect of the invention relates to a polynucleotide comprising at least one synthetic adeno-associated virus (AAV) inverted terminal repeat (ITR), wherein said ITR comprises, consists essentially of, or consists of; (a) an AAV rep binding element; (b) an AAV terminal resolution sequence; and (c) an AAV RBE' element; wherein said ITR does not comprise any other AAV ITR sequences. In some embodiments, elements (a), (b), and (c) are from AAV2 ITR and the synthetic ITR does not comprise any other AAV2 ITR sequences. In some embodiments, the polynucleotide comprises two synthetic ITRs, which may be the same or different. The three elements in the ITR have been determined to be sufficient for ITR function. This minimal functional ITR can be used in all aspects of AAV vector production and transduction. Additional deletions may define an even smaller minimal functional ITR. The shorter length advantageously permits the packaging and transduction of larger transgenic cassettes.

The sequence of the rep binding element, terminal resolution sequence, and RBE' element of AAV ITRs are well known in the art. The elements in AAV2 ITR are shown in FIG. 1. Each of the elements as present in the synthetic ITR can be the exact sequence as exists in a naturally occurring AAV ITR or can differ slightly (e.g., differ by addition, deletion, and/or substitution of 1, 2, 3, 4 or 5 nucleotides) as long as the function of the element is not substantially different from the function of the element as it exists in the naturally occurring AAV ITR, The term "substantially different" is defined herein as a difference in function (e.g., transduction efficiency) of greater than 50%.

The phrase "does not comprise any other ITR sequences" as used herein means that the ITR does not contain any other structural or functional elements found in a naturally occurring AAV ITR and does not contain a sequence of 6 or more contiguous nucleotides that is found in a naturally occurring AAV ITR, e.g., 8, 10, or 12 or more contiguous nucleotides.

In certain embodiments, the ITR may further comprise additional non-AAV cis elements, e.g., elements that initiate transcription, mediate enhancer function, allow replication and symmetric distribution upon mitosis, or alter the persistence and processing of transduced genomes. Such elements are well known in the art and include, without limitation, promoters, enhancers, chromatin attachment sequences, telomeric sequences, cis-acting microRNAs, and combinations thereof.

In certain embodiments, the ITR exhibits modified transcription activity relative to a naturally occurring ITR, e.g., ITR2. It is known that the ITR2 sequence inherently has promoter activity. It also inherently has termination activity, similar to a poly(A) sequence. The minimal functional ITR of the present invention exhibits transcription activity as shown in the examples, although at a diminished level relative to ITR2. Thus, in some embodiments, the ITR is functional for transcription. In other embodiments, the ITR is defective for transcription. In certain embodiments, the ITR can act as a transcription insulator, e.g., prevent transcription of a transgenic cassette present in the vector when the vector is integrated into a host chromosome.

Figure 2:
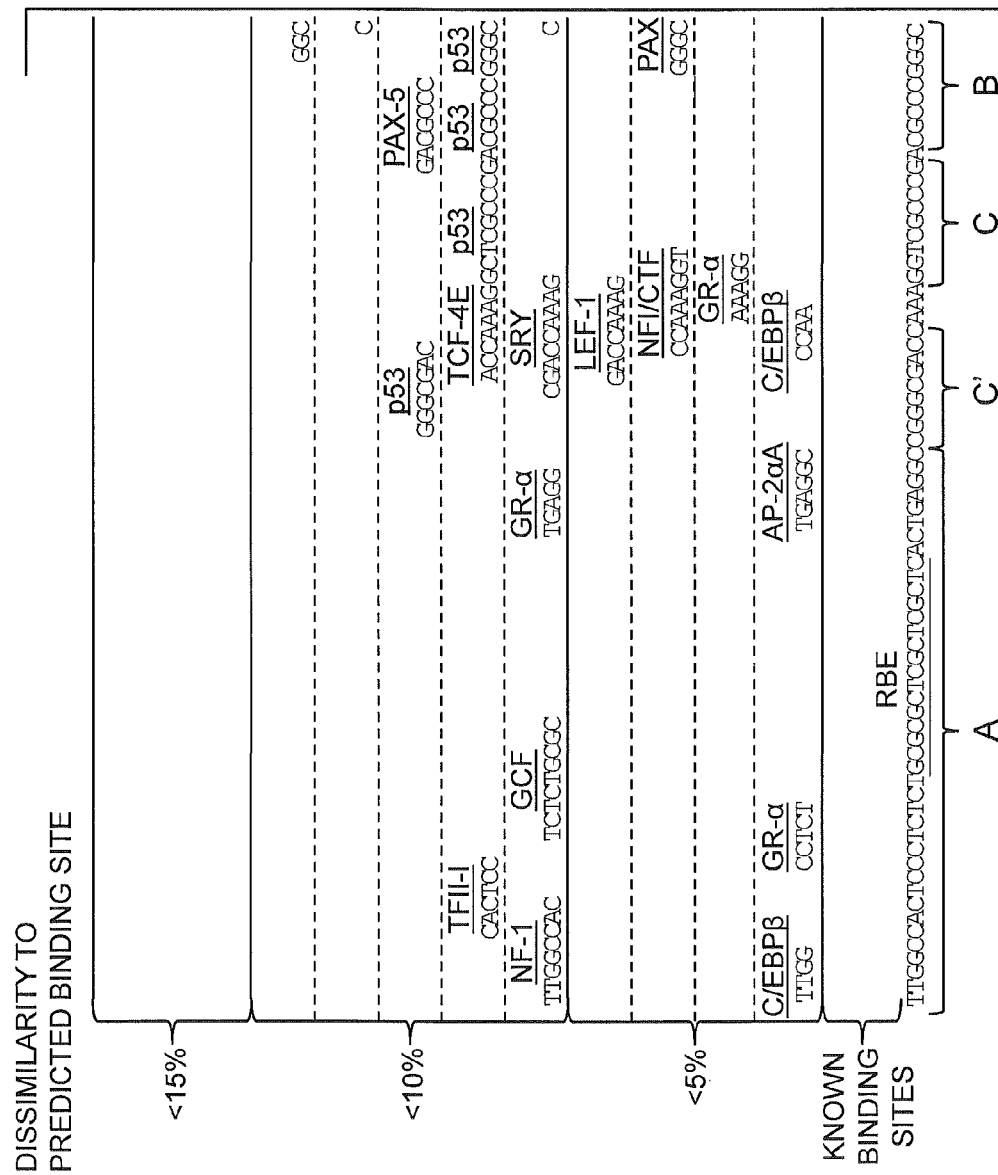
FIG. 2 shows a map of the putative transcription factor binding sites in AAV2 ITR (SEQ ID NO:9).
Figure 2:
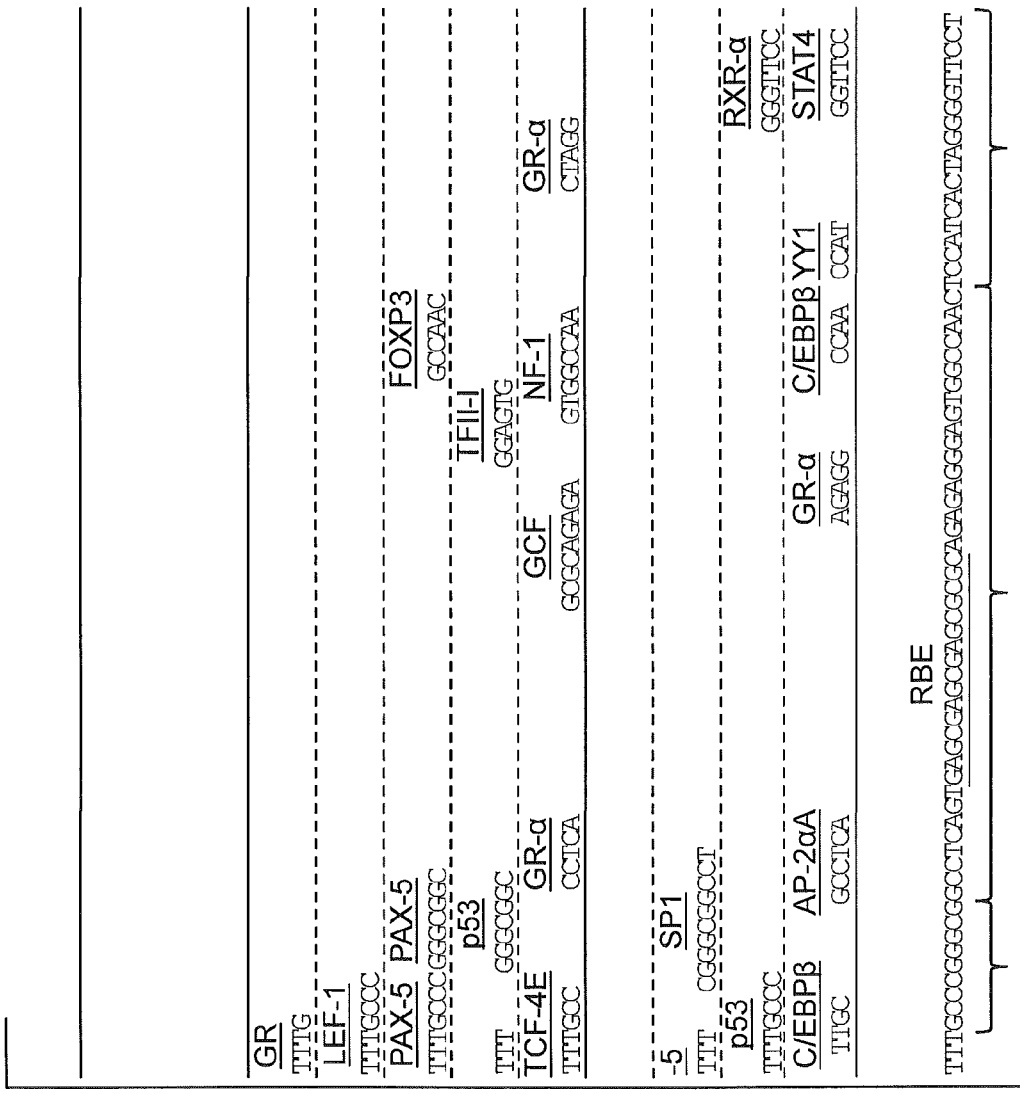

One aspect of the invention relates to a polynucleotide comprising at least one synthetic AAV ITR, wherein the nucleotide sequence of one or more transcription factor binding sites in the ITR is deleted and/or substituted, relative to the sequence of a naturally occurring AAV ITR such as ITR2. In some embodiments, it is the minimal functional ITR in which one or more transcription factor binding sites are deleted and/or substituted. The AAV ITR2 contains 21 putative transcription factor binding sites as shown in FIG. 2. In some embodiments at least 1 transcription factor binding site is deleted and/or substituted, e.g., at least 5 or more or 10 or more transcription factor binding sites, e.g., at least 1, 2, 3, 4, 5, 6, 7, 8, 9, 10, 11, 12, 13, 14, 15, 16, 17, 18, 19, 20, or 21 transcription factor binding sites. The phrase "deleted and/or substituted" as used herein means that at least 1 nucleotide, e.g., at least 2 or 3 nucleotides, in the transcription factor binding site is deleted, substituted with a nucleotide that is not normally present in the binding site, or any combination of deletions and substitutions. In certain embodiments, the deletion and/or substitution renders the binding site non-functional, i.e., no longer capable of binding its cognate transcription factor. Nucleotide deletions and substitutions that render a transcription factor binding site non-functional are well known in the art and can be readily determined by one of skill in the art.

Because the synthetic ITRs have missing and/or non-functional transcription factor binding sites, vectors comprising the synthetic ITRs produced an altered transcriptional response in important regulatory cascades in host cells into which they are transduced. Synthetic ITRs can be generated that alter different pathways depending on which binding sites are inactivated.

In some embodiments, the synthetic ITR does not induce apoptosis in a host cell, e.g., in stem cells or cancer cells, as ITR2 has been reported to do.

In some embodiments, the ITR elicits altered p53 activation when transduced into a host cell.

In some embodiments, the synthetic ITR elicits altered cell cycle progression when transduced into a host cell.

In some embodiments, the synthetic ITR elicits altered DNA damage response when transduced into a host cell.

In certain embodiments, the synthetic ITR is enhanced for intra- or inter-molecular homologous recombination.

In certain embodiments, the synthetic ITR exhibits increased host chromosome integration of transduced vector genomes. In other embodiments, the ITR exhibits decreased host chromosome integration of transduced vector genomes.

One aspect of the invention relates to a polynucleotide comprising at least one synthetic AAV ITR, wherein one or more CpG motifs in said ITR are deleted and/or substituted, relative to the sequence of a naturally occurring AAV ITR such as ITR2. In some embodiments, it is the minimal functional ITR in which one or more CpG motifs are deleted and/or substituted. The AAV ITR2 contains 16 CpG motifs, TLR-9 directly binds to CpG sequence motifs and results in the activation of cellular innate immunity. It is also well known that methylation of CpG motifs results in transcriptional silencing. Removal of CpG motifs in the ITR is expected to result in decreased TLR-9 recognition and/or decreased methylation and therefore decreased transgene silencing.

In some embodiments at least 1 CpG motif is deleted and/or substituted, e.g., at least 4 or more or 8 or more CpG motifs, e.g., at least 1, 2, 3, 4, 5, 6, 7, 8, 9, 10, 11, 12, 13, 14, 15, or 16 CpG motifs. The phrase "deleted and/or substituted" as used herein means that one or both nucleotides in the CpG motif is deleted, substituted with a different nucleotide, or any combination of deletions and substitutions.

In some embodiments, the synthetic ITR comprises, consists essentially of, or consists of one of the nucleotide sequences listed below. In each of the sequences, the RBE element is indicated in italics, the terminal resolution sequence is indicated in bold, and the RBE' element is underlined. In other embodiments, the synthetic ITR comprises, consist essentially of, or consist of a nucleotide sequence that is at least 80% identical, e.g., at least 85%, 90%, 95%, 96%, 97%, 98%, or 99% identical to one of the nucleotide sequences listed below. The predicted structure of the MH-257, MH-258, and MH Delta 258 ITRs is shown in FIG. 5 and a sequence alignment of the three ITRs with ITR2 is shown in FIG. 6.

MH-257
(SEQ ID NO:1)
AGGAACCCCTAGTGATGGAGTTGGCCACTCCCTCTCTGCGCGCTCGCTCG

CTCACTGAGGCAATTTGATAAAAATCGTCAAATTATAAACAGGCTTTGCC

TGTTTAGCCTCAGTGAGCGAGCGAGCGCGCAGAGAGGGAGTGGCCAACTC

CATCACTAGGGGTTCCT

MH-258
(SEQ ID NO:2)
AGGAACCCCTAGTGATGGAGTTGGCCACTCCCTCTCTGCGCGCTCGCTCG

CTCACTGAGGGATAAAAATCCAGGCTTTGCCTGCCTCAGTGAGCGAGCGA

GCGCGCAGAGAGGGAGTGGCCAACTCCATCACTAGGGGTTCCT

MH Delta 258
(SEQ ID NO:3)
AGGAACCCCTAGTGATGGAGTTGGCCACTCCCTCTCTGCGCGCTCGCTCG

CTCACTGAGGGATAAAAATCCAGGCTTTGCCTGCCTCAGTGAGCGAGCGA

GCGCGCAGAGAGGGAGTGGCCAACTCCATCACTAGGGGTTCCT

MH Telomere-1 ITR
(SEQ ID NO:4)
AGGAACCCCTAGTGATGGAGTTGGCCACTCCCTCTCTGGGATTGGGATTG

CGCGCTCGCTCGCGGGATTGGGATTGGGATTGGGATTGGGATTGGGATTG

ATAAAAATCAATCCCAATCCCAATCCCAATCCCAATCCCAATCCCGCGAG

CGAGCGCGCAATCCCAATCCCAGAGAGGGAGTGGCCAACTCCATCACTAG

GGGTTCCT

MH Telomere-2 ITR
(SEQ ID NO:5)
AGGAACCCCTAGTGATGGAGTTGGCCACTCCCTCTCTGCGCGCTCGCTCG

CTCGGGATTGGGATTGGGATTGGGATTGGGATTGGGATTGATAAAAATCA

ATCCCAATCCCAATCCCAATCCCAATCCCAATCCCGCGAGCGAGCGCGCA

GGAGAGGGAGTGGCCAACTCCATCACTAGGGGTTCCTAAGCTTATTATA

MH PolII 258 ITR
(SEQ ID NO:6)
AGGAACCCCTAGTGATGGAGTTGGCCACTCCCTCTCTGCGCGCTCGCTCG

CTCACTGAGGGCGCCTATAAAGATAAAAATCCAGGCTTTGCCTGCCTCAG

TTAGCGAGCGAGCGCGCAGAGAGGGAGTGGCCAACTCCATCACTAGGGGT

TCCT

MH 258 Delta D conservative
(SEQ ID NO:7)
CTAGTGATGGAGTTGGCCACTCCCTCTCTGCGCGCTCGCTCGCTCACTGA

GGGATAAAAATCCAGGCTTTGCCTGCCTCAGTGAGCGAGCGAGCGCGCAG

AGAGGGAGTGGCCAACTCCATCACTAG

In certain embodiments, a polynucleotide containing the synthetic ITR is capable of producing AAV virus particles that can transduce host cells. Such ITRs can be used, for example, for viral delivery of heterologous nucleic acids. Examples of such ITRs include MH-257, MH-258, and MH Delta 258 listed above.

In other embodiments, a polynucleotide containing the synthetic ITR is not capable of producing AAV virus particles. Such ITRs can be used, for example, for non-viral transfer of heterologous nucleic acids. Examples of such ITRs include MH Telomere-1, MH Telomere-2, and MH PolII 258 listed above.

In one aspect of the invention the polynucleotide comprising the synthetic ITR of the invention further comprises a second ITR which may be the same as or different from the first ITR. In one embodiment, the polynucleotide further comprises a heterologous nucleic acid, e.g., a sequence encoding a protein or a functional RNA. In some embodiments, the second ITR cannot be resolved by the Rep protein, i.e., resulting in a double stranded viral DNA.

The invention also provides a viral vector comprising the polynucleotide comprising the synthetic ITR of the invention. The viral vector can be a parvovirus vector, e.g., an AAV vector. The invention further provides a recombinant parvovirus particle (e.g., a recombinant AAV particle) comprising the synthetic ITR of the invention. Viral vectors and viral particles are discussed further below.

Another aspect of the invention relates to a method of increasing the transgenic DNA packaging capacity of an AAV vector, comprising generating a vector comprising at least one synthetic AAV ITR, wherein said ITR comprises: (a) an AAV rep binding element; (b) an AAV terminal resolution sequence; and (c) an AAV RBE' element; wherein said ITR does not comprise any other AAV ITR sequences.

A further aspect of the invention relates to a method of altering the cellular response to infection by an AAV vector, comprising generating a vector comprising at least one synthetic ITR, wherein the nucleotide sequence of one or more transcription factor binding sites in said ITR is deleted and/or substituted, wherein the vector comprising at least one synthetic ITR produces an altered cellular response to infection.

An additional aspect of the invention relates to a method of altering the cellular response to infection by an AAV vector, comprising generating a vector comprising at least one synthetic ITR, wherein one or more CpG motifs in said ITR are deleted and/or substituted, wherein the vector comprising at least one synthetic ITR produces an altered cellular response to infection.

Methods of Producing Virus Vectors

The present invention further provides methods of producing virus vectors. In one particular embodiment, the present invention provides a method of producing a recombinant AAV particle, comprising providing to a cell permissive for AAV replication: (a) a recombinant AAV template comprising (i) a heterologous nucleotide sequence, and (ii) the synthetic ITR of the invention; (b) a polynucleotide comprising Rep coding sequences and Cap coding sequences; under conditions sufficient for the replication and packaging of the recombinant AAV template; whereby recombinant AAV particles are produced in the cell. Conditions sufficient for the replication and packaging of the recombinant AAV template can be, e.g., the presence of AAV sequences sufficient for replication of the AAV template and encapsidation into AAV capsids (e.g., AAV rep sequences and AAV cap sequences) and helper sequences from adenovirus and/or herpesvirus. In particular embodiments, the AAV template comprises two AAV ITR sequences, which are located 5' and 3' to the heterologous nucleic acid sequence, although they need not be directly contiguous thereto.

In some embodiments, the recombinant AAV template comprises an ITR that is not resolved by Rep to make duplexed AAV vectors as described in international patent publication WO 01/92551.

The AAV template and AAV rep and cap sequences are provided under conditions such that virus vector comprising the AAV template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell (e.g., a primate or human cell). As another option, the cell can be a trans-complementing packaging cell line that provide functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) Curr. Top. Microbiol. Immun. 158: 67).

As a further alternative, the rep/cap sequences may be stably incorporated into a cell.

Typically the AAV rep/cap sequences will not be flanked by the TRs, to prevent rescue and/or packaging of these sequences.

The AAV template can be provided to the cell using any method known in the art. For example, the template can be supplied by a non-viral (e.g., plasmid) or viral vector. In particular embodiments, the AAV template is supplied by a herpesvirus or adenovirus vector (e.g., inserted into the E1a or E3 regions of a deleted adenovirus). As another illustration, Palombo et al., (1998) J. Virology 72:5025, describes a baculovirus vector carrying a reporter gene flanked by the AAV TRs. EBV vectors may also be employed to deliver the template, as described above with respect to the rep/cap genes.

In another representative embodiment, the AAV template is provided by a replicating rAAV virus. In still other embodiments, an AAV provirus comprising the AAV template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al., (1997) Nature Med. 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by ITRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector can further comprise the AAV template. The AAV rep/cap sequences and/or the AAV template can be inserted into a deleted region (e.g., the E1a or E3 regions) of the adenovirus.

In a further embodiment, the AAV rep/cap sequences and the adenovirus helper sequences are supplied by a single adenovirus helper vector. According to this embodiment, the AAV template can be provided as a plasmid template.

In another illustrative embodiment, the AAV rep/cap sequences and adenovirus helper sequences are provided by a single adenovirus helper vector, and the AAV template is integrated into the cell as a provirus. Alternatively, the AAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The AAV template can be provided as a separate replicating viral vector. For example, the AAV template can be provided by a AAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the AAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by ITRs so that these sequences are not packaged into the AAV virions.

Zhang et al., ((2001) *Gene Ther.* 18:704-12) describe a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al., (1999) *Gene Ther.* 6:986 and WO 00/17377.

As a further alternative, the virus vectors of the invention can be produced in insect cells using baculovirus vectors to deliver the rep/cap genes and AAV template as described, for example, by Urabe et al., (2002) *Human Gene Ther.* 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV. Adenovirus mutants defective for late gene expression are known in the art (e.g., ts100K and ts149 adenovirus mutants).

Recombinant Virus Vectors

The virus vectors of the present invention are useful for the delivery of nucleic acids to cells in vitro, ex vivo, and in vivo. In particular, the virus vectors can be advantageously employed to deliver or transfer nucleic acids to animal, including mammalian, cells.

Any heterologous nucleic acid sequence(s) of interest may be delivered in the virus vectors of the present invention. Nucleic acids of interest include nucleic acids encoding polypeptides, including therapeutic (e.g., for medical or veterinary uses), immunogenic (e.g., for vaccines), or diagnostic polypeptides.

Therapeutic polypeptides include, but are not limited to, cystic fibrosis transmembrane regulator protein (CFTR), dystrophin (including mini- and micro-dystrophins (see, e.g., Vincent et al., (1993) *Nature Genetics* 5:130; U.S. Patent Publication No. 2003/017131; International publication WO/2008/088895, Wang et al., *Proc. Natl. Acad. Sci. USA* 97:13714-13719 (2000); and Gregorevic et al., *Mol.* *Ther.* 16:657-64 (2008)), myostatin propeptide, follistatin, activin type II soluble receptor, IGF-1, anti-inflammatory polypeptides such as the Ikappa B dominant mutant, sarcospan, utrophin (Tinsley et al., (1996) *Nature* 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $\alpha_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), lysosomal acid α-glucosidase, α-galactosidase A, receptors (e.g., the tumor necrosis growth factor α soluble receptor), S100A1, parvalbumin, adenylyl cyclase type 6, a molecule that effects G-protein coupled receptor kinase type 2 knockdown such as a truncated constitutively active bARKct, anti-inflammatory factors such as IRAP, anti-myostatin proteins, aspartoacylase, and monoclonal antibodies (including single chain monoclonal antibodies; an exemplary Mab is the Herceptin® Mab). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. AAV vectors can also be used to deliver monoclonal antibodies and antibody fragments, for example, an antibody or antibody fragment directed against myostatin (see, e.g., Fang et al., *Nature Biotechnol.* 23:584-590 (2005)).

Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Alternatively, in particular embodiments of this invention, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. No. 6,013,487; U.S. Pat. No. 6,083,702), interfering RNAs (RNAi) including siRNA, shRNA or miRNA that mediate gene silencing (see, Sharp et al., (2000) *Science* 287:2431), and other non-translated RNAs, such as "guide" RNAs (Gorman et al., (1998) *Proc. Nat. Acad. Sci. USA* 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al., *J. Gene Med.* 10:132-142 (2008) and Li et al., *Acta Pharmacol Sin.* 26:51-55 (2005)); phospholamban inhibitory or dominant-negative molecules such as phospholamban S16E (e.g., to treat cardiovascular disease, see, e.g., Hoshijima et al. *Nat. Med.* 8:864-871 (2002)), RNAi to adenosine kinase (e.g., for epilepsy), RNAi to a sarcoglycan [e.g., α, β, γ], RNAi against myostatin, myostatin propeptide, follistatin, or activin type II soluble receptor, RNAi against anti-inflammatory polypeptides such as the Ikappa B dominant mutant, and RNAi directed against pathogenic organisms and viruses (e.g., hepatitis B virus, human immunodeficiency virus, CMV, herpes simplex virus, human papilloma virus, etc.).

Alternatively, in particular embodiments of this invention, the heterologous nucleic acid may encode protein phosphatase inhibitor I (I-1), serca2a, zinc finger proteins that regulate the phospholamban gene, Barkct, β2-adrenergic receptor, β2-adrenergic receptor kinase (BARK), phosphoinositide-3 kinase (PI3 kinase), a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, enos, inos, or bone morphogenic proteins (including BNP 2, 7, etc., RANKL and/or VEGF).

The virus vector may also comprise a heterologous nucleic acid that shares homology with and recombines with a locus on a host chromosome. This approach can be utilized, for example, to correct a genetic defect in the host cell.

The present invention also provides virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of AAV as vaccine vectors is known in the art (see, e.g., Miyamura et al., (1994) *Proc. Nat. Acad. Sci USA* 91:8507; U.S. Pat. No. 5,916,563 to Young et al., U.S. Pat. No. 5,905,040 to Mazzara et al., U.S. Pat. No. 5,882,652, U.S. Pat. No. 5,863,541 to Samulski et al.). The antigen may be presented in the AAV capsid. Alternatively, the antigen may be expressed from a heterologous nucleic acid introduced into a recombinant vector genome. Any immunogen of interest as described herein and/or as is known in the art can be provided by the virus vector of the present invention.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP 160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg (*Immunity* 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.,* 180:347; Kawakami et al., (1994) *Cancer Res.* 54:3124), MART-1, gp100 MAGE-1, MAGE-2, MAGE-3, CEA, TRP-1, TRP-2, P-15, tyrosinase (Brichard et al., (1993) *J. Exp. Med.* 178: 489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg, (1996) *Ann. Rev. Med.* 47:481-91).

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Those skilled in the art will appreciate that a variety of promoter/enhancer elements can be used depending on the level and tissue-specific expression desired. The promoter/ enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present invention can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic defects, congenital emphysema (α1-antitrypsin), Lesch-Nyhan Syndrome (hypoxanthine guanine phosphoribosyl transferase), Niemann-Pick disease (sphingomyelinase), Tays Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1), serca2a, zinc finger proteins that regulate the phospholamban gene, Barkct, β2-adrenergic receptor, β2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present invention permit the treatment and/or prevention of genetic diseases.

The virus vectors according to the present invention may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

Virus vectors according to the instant invention find use in diagnostic and screening methods, whereby a nucleic acid of interest is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present invention may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, Immunophysiology: Cell Function and Cellular Interactions in Antibody Formation, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, interleukin-2) from an actively immunized host to a nonimmune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector or cell comprising the heterologous nucleic acid can be administered in an immunogenically effective amount, as described below.

The virus vectors of the present invention can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein. Alternatively, the cancer antigen can be expressed as part of the virus capsid or be otherwise associated with the virus capsid as described above.

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the invention provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a virus vector according to the instant invention. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, β-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration

Virus vectors and capsids according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles and adults.

In particular embodiments, the present invention provides a pharmaceutical composition comprising a virus vector and/or capsid of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, more preferably at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendrocytes), lung cells, cells of the eye (including retinal cells, retinal pigment epithelium, and corneal cells), blood vessel cells (e.g., endothelial cells, intimal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, kidney cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo gene delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vector to subjects. Administration of the virus vectors and/or capsids according to the present invention to a human subject or an animal in need thereof can be by any means known in the art. Optionally, the virus vector and/or capsid is delivered in a treatment effective or prevention effective dose in a pharmaceutically acceptable carrier.

The virus vectors and/or capsids of the invention can further be administered to elicit an immunogenic response (e.g., as a vaccine). Typically, immunogenic compositions of the present invention comprise an immunogenically effective amount of virus vector and/or capsid in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$ transducing units, optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, intraendothelial, in utero (or in ovo), parenteral (e.g., intravenous, subcutaneous, intradermal, intracranial, intramuscular [including administration to skeletal, diaphragm and/or cardiac muscle], intrapleural, intracerebral, and intraarticular), topical (e.g., to both skin and mucosal surfaces, including airway surfaces, and transdermal administration), intralymphatic, and the like, as well as direct tissue or organ injection (e.g., to liver, eye [including intravitreal and subretinal], skeletal muscle, cardiac muscle, diaphragm muscle or brain).

Administration can be to any site in a subject, including, without limitation, a site selected from the group consisting of the brain, a skeletal muscle, a smooth muscle, the heart, the diaphragm, the airway epithelium, the liver, the kidney, the spleen, the pancreas, the skin, and the eye.

Administration can also be to a tumor (e.g., in or near a tumor or a lymph node). The most suitable route in any given case will depend on the nature and severity of the condition being treated and/or prevented and on the nature of the particular vector that is being used.

Administration to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficialis, flexor hallucis brevis, flexor hallucis longus, flexor pollicis brevis, flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor, and any other suitable skeletal muscle as known in the art.

The virus vector can be delivered to skeletal muscle by intravenous administration, intra-arterial administration, intraperitoneal administration, limb perfusion, (optionally, isolated limb perfusion of a leg and/or arm; see, e.g. Arruda et al., (2005) *Blood* 105: 3458-3464), and/or direct intramuscular injection. In particular embodiments, the virus vector and/or capsid is administered to a limb (arm and/or leg) of a subject (e.g., a subject with muscular dystrophy such as DMD) by limb perfusion, optionally isolated limb perfusion (e.g., by intravenous or intra-articular administration. In embodiments of the invention, the virus vectors and/or capsids of the invention can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In particular embodiments, the viral vectors and/or capsids of the invention can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intraperitoneal administration.

Administration to smooth muscle can be by any suitable method including intravenous administration, intra-arterial administration, and/or intra-peritoneal administration. In one embodiment, administration can be to endothelial cells present in, near, and/or on smooth muscle.

Delivery to a target tissue can also be achieved by delivering a depot comprising the virus vector and/or capsid. In representative embodiments, a depot comprising the virus vector and/or capsid is implanted into skeletal, smooth, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector according to the present invention is administered to skeletal muscle, diaphragm muscle and/or cardiac muscle (e.g., to treat and/or prevent muscular dystrophy or heart disease [for example, PAD or congestive heart failure]).

In representative embodiments, the invention is used to treat and/or prevent disorders of skeletal, cardiac and/or diaphragm muscle.

In a representative embodiment, the invention provides a method of treating and/or preventing muscular dystrophy in a subject in need thereof, the method comprising: administering a treatment or prevention effective amount of a virus vector of the invention to a mammalian subject, wherein the virus vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-α2, α-sarcoglycan, β-sarcoglycan, γ-sarcoglycan, β-sarcoglycan, IGF-1, an antibody or antibody fragment against myostatin or myostatin propeptide, and/or RNAi against myostatin. In particular embodiments, the virus vector can be administered to skeletal, diaphragm and/or cardiac muscle as described elsewhere herein.

Alternatively, the invention can be practiced to deliver a nucleic acid to skeletal, cardiac or diaphragm muscle, which is used as a platform for production of a polypeptide (e.g., an enzyme) or functional RNA (e.g., RNAi, microRNA, antisense RNA) that normally circulates in the blood or for systemic delivery to other tissues to treat and/or prevent a disorder (e.g., a metabolic disorder, such as diabetes (e.g., insulin), hemophilia (e.g., Factor IX or Factor VIII), a mucopolysaccharide disorder (e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.) or a lysosomal storage disorder (such as Gaucher's disease [glucocerebrosidase], Pompe disease [lysosomal acid α-glucosidase] or Fabry disease [α-galactosidase A]) or a glycogen storage disorder (such as Pompe disease [lysosomal acid α glucosidase]). Other suitable proteins for treating and/or preventing metabolic disorders are described above. The use of muscle as a platform to express a nucleic acid of interest is described in U.S. Patent Publication No. 2002/0192189.

Thus, as one aspect, the invention further encompasses a method of treating and/or preventing a metabolic disorder in a subject in need thereof, the method comprising: administering a treatment or prevention effective amount of a virus vector of the invention to a subject (e.g., to skeletal muscle of a subject), wherein the virus vector comprises a heterologous nucleic acid encoding a polypeptide, wherein the metabolic disorder is a result of a deficiency and/or defect in the polypeptide. Illustrative metabolic disorders and heterologous nucleic acids encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art). Without being limited by any particular theory of the invention, according to this embodiment, administration to the skeletal muscle can result in secretion of the polypeptide into the systemic circulation and delivery to target tissue(s). Methods of delivering virus vectors to skeletal muscle are described in more detail herein.

The invention can also be practiced to produce antisense RNA, RNAi or other functional RNA (e.g., a ribozyme) for systemic delivery.

The invention also provides a method of treating and/or preventing congenital heart failure or PAD in a subject in need thereof, the method comprising administering a treatment or prevention effective amount of a virus vector of the invention to a mammalian subject, wherein the virus vector comprises a heterologous nucleic acid encoding, for example, a sarcoplasmic endoreticulum $Ca^{2+}$-ATPase (SERCA2a), an angiogenic factor, phosphatase inhibitor I (I-1), RNAi against phospholamban; a phospholamban inhibitory or dominant-negative molecule such as phospholamban S16E, a zinc finger protein that regulates the phospholamban gene, β2-adrenergic receptor, β2-adrenergic receptor kinase (BARK), PI3 kinase, calsarcan, a β-adrenergic receptor kinase inhibitor (βARKct), inhibitor 1 of protein phosphatase 1, S100A1, parvalbumin, adenylyl cyclase type 6, a molecule that effects G-protein coupled receptor kinase type 2 knockdown such as a truncated constitutively active bARKct, Pim-1, PGC-1α, SOD-1, SOD-2, EC-SOD, kallikrein, HIF, thymosin-β4, mir-1, mir-133, mir-206 and/or mir-208.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. 2004-0013645).

The virus vectors disclosed herein can be administered to the lungs of a subject by any suitable means, optionally by administering an aerosol suspension of respirable particles comprised of the virus vectors and/or virus capsids, which the subject inhales. The respirable particles can be liquid or solid. Aerosols of liquid particles comprising the virus vectors and/or virus capsids may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors and/or capsids may likewise be produced with any solid particulate medicament aerosol generator, by techniques known in the pharmaceutical art.

The virus vectors can be administered to tissues of the CNS (e.g., brain, eye) and may advantageously result in broader distribution of the virus vector or capsid than would be observed in the absence of the present invention.

In particular embodiments, the delivery vectors of the invention may be administered to treat diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally or subretinally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive delivery vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present invention may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a delivery vector of the invention to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins are known in the art.

In particular embodiments, the vector can comprise a secretory signal as described in U.S. Pat. No. 7,071,172.

In representative embodiments of the invention, the virus vector and/or virus capsid is administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes. cortex, basal ganglia, hippocampus and portaamygdala), limbic system, neocortex, corpus striatum, cerebrum, and inferior colliculus. The virus vector and/or capsid may also be administered to different regions of the eye such as the retina, cornea and/or optic nerve.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intraocular (e.g., intra-vitreous, sub-retinal, anterior chamber) and peri-ocular (e.g., sub-Tenon's region) delivery as well as intramuscular delivery with retrograde delivery to motor neurons.

In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye, may be by topical application of liquid droplets. As a further alternative, the virus vector and/or capsid may be administered as a solid, slow-release formulation (see, e.g., U.S. Pat. No. 7,201, 898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

Having described the present invention, the same will be explained in greater detail in the following examples, which are included herein for illustration purposes only, and which are not intended to be limiting to the invention.

Example 1

Development of Synthetic ITRs

AAV vector technology currently uses the 145 nucleotide ITRs from AAV serotype 2 which contain several putative transcription factor binding sites (FIGS. 1 and 3). To engineer synthetic ITRs with substitutions and/or deletion of these sites we employed a novel cloning strategy based on amplification of oligonucleotide sequences and then a triple DNA molecule ligation. This strategy relies on ITR generation via the A/T nucleotide BsaB1 endonuclease sequence which, unlike the ITR production scheme of Hewitt et al., inherently does not have any known regulation sites (FIG. 4)[5]. Also considered in our ITR design was the definition of the minimal requirements for AAV vector production (genome replication and packaging), as well as the overall CpG content which is associated with AAV methylation, silencing and thus transgene persistence [11-16].

Figure 4:
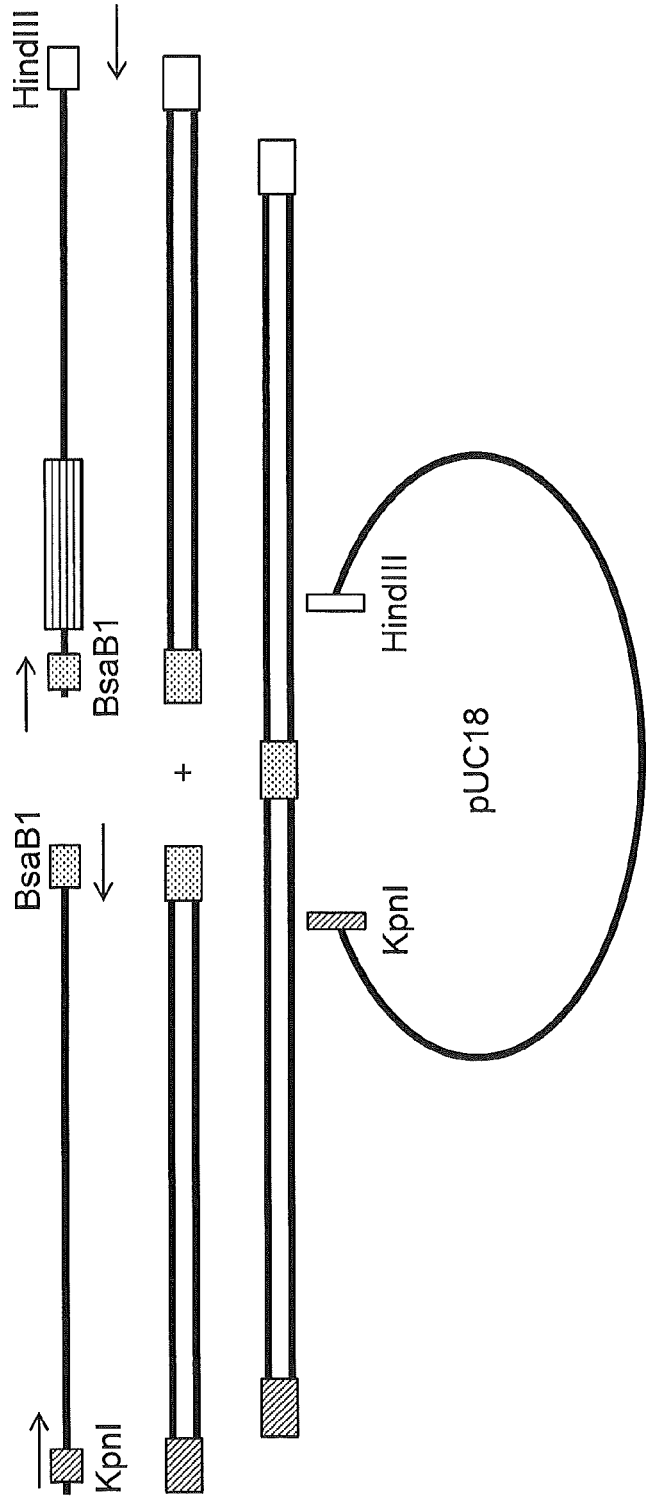
FIG. 4 shows the cloning strategy for synthetic ITRs.

All ITRs were created as depicted in FIG. 4. Briefly, 2 PCR reactions using purchased Ultramers (IDT) as templates were performed. The amplification generated a HindIII or Kpn site in addition to a BsaB1 site on each amplicon. A triple ligation was then performed as depicted in FIG. 4. Plasmids were propagated in recombination deficient bacteria using standard protocols and verified by sequencing of BsaB1 digested products. AAV vector production relied on a well published protocol developed by the Samulski lab that relies on a triple plasmid transfection of 293 cells and viral vector purification by one of several methods. Vector titers were determined using Q-PCR. The AAV serotype 2 capsid was used for packaging in all instances except when the vector was administered intravenously in which case AAV8 was used.

Some of the synthetic ITRs generated thus far are depicted in FIGS. 5 and 6 and include the following: i) ITR-257 contains substitution of the putative transcription factor binding sites and is deleted for 8 CpG of the 16 CpG motifs found in ITR2, ii) ITR-258 is deleted for several putative transcription factor binding sites, exhibits 8 CpG motifs and is 22 nucleotides smaller than the ITR2 sequence, and iii) ITR-261 contains an additional ITR deletion compared to ITR-258 (52 nucleotides less than ITR2) and 8 CpG motifs (FIGS. 3, 5, and 6). AAV vector production using plasmids generated with ITR-257 and ITR-258 resulted in similar titers compared to AAV ITR2, in an AAV capsid independent manner, demonstrating that the molecular requirements for vector generation are satisfied. In contrast, ITR-261 was not able to produce AAV vectors possibly due to the loss of the RBE' element which was reported as a necessary secondary contact for the AAV Rep protein during the initiation of viral genome replication [16].

Example 2

In Vitro Transduction with Synthetic ITRs

The synthetic AAV vectors containing ITR2-257 and ITR-258 sequences were next investigated for transduction in vitro using a CMV-eGFP cassette. The in vitro experiments utilized 2 cell lines (ATCC) that are diploid representatives of either human (normal human fibroblasts or NHF) and mouse cells (C2C12 myoblasts). A vector cell ratio of 10,000 was used unless otherwise indicated and the AAV2 capsid was used in all cases. Three days post-infection cells were observed by microscopy and harvested for % GFP+ cell quantitation by flow cytometry.

In human fibroblasts, both of the synthetic ITRs were competent for transduction with ITR-258 vectors increased 2-3 fold compared to the traditional ITR2 vectors (FIG. 7A). Curiously, this profile was not maintained in mouse C2C12 myoblasts in which ITR-257 vector transduction demonstrated a 2-fold reduction in GFP+ cells compared to AAV ITR2 (FIG. 7C). However, the decreased transduction efficiency was not observed with the ITR-258 vectors which demonstrated a similar 2-fold enhancement over AAV ITR2 based vectors (FIGS. 7B and 7D). These results demonstrate that synthetic ITR sequences can confer species dependent transduction (ITR-257), or can consistently enhance AAV vector transduction, compared to the traditional AAV2 ITR.

Example 3

In Vivo Transduction with Synthetic ITRs

To investigate whether the synthetic ITR vectors mediate transduction in vivo, ITR-257 and ITR-258 were administered to the tibialis anterior (TA) muscle of WT B6 mice. For the muscle experiments, $1 \times 10^9$ of the indicated viral genomes were injected directly into the tibialis anterior in a volume of 80 Two weeks post-injection, the injected muscles were recovered, lysed and GFP protein abundance was determined by Western blot using a mouse anti-GFP antibody (SantaCruz).

Figure 8A:
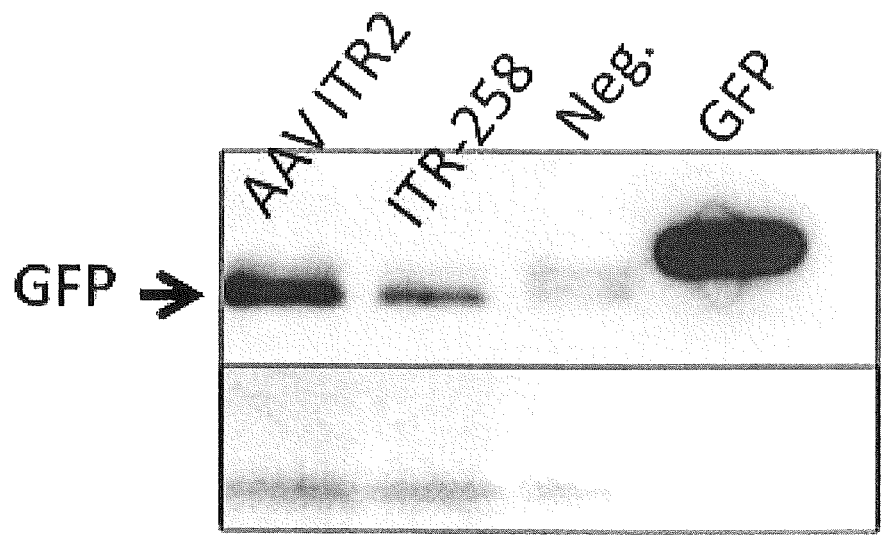
FIGS. 8A-8B show synthetic ITR vector transduction in vivo. $1 \times 10^9$ viral genomes of CMV-eGFP vectors containing the indicated ITRs were administered to the TA muscle of WT mice. Western blotting for GFP was performed 2 weeks post-injection.
Figure 8B:
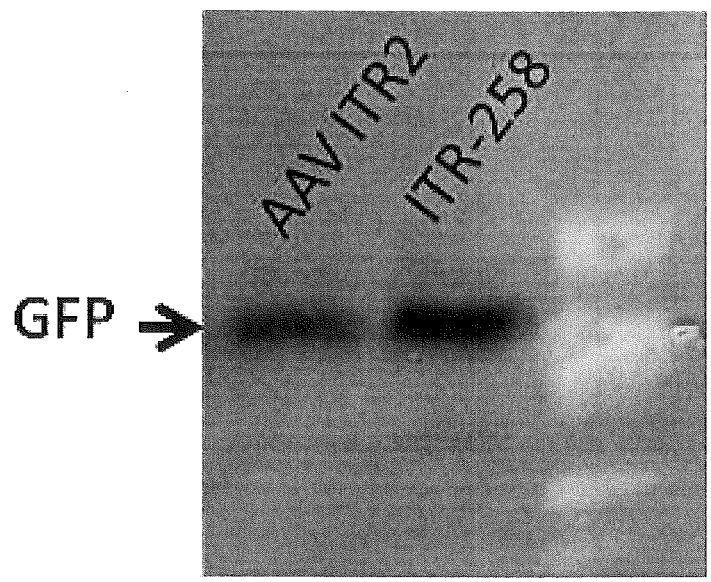

The results using ITR-257 vectors were consistent to the transduction results in the mouse myoblast culture (FIGS. 7 and 8). In this case, GFP abundance was significantly decreased 3-fold compared to the transduction mediated by AAV ITR2s. In contrast, GFP was elevated approximately 2-fold in the skeletal muscle treated with ITR-258 vectors compared to the AAV ITR2 control (FIG. 8). These results are consistent to the performance of ITR-258 in both human and mouse cell culture (FIGS. 7 and 8).

Figure 9:
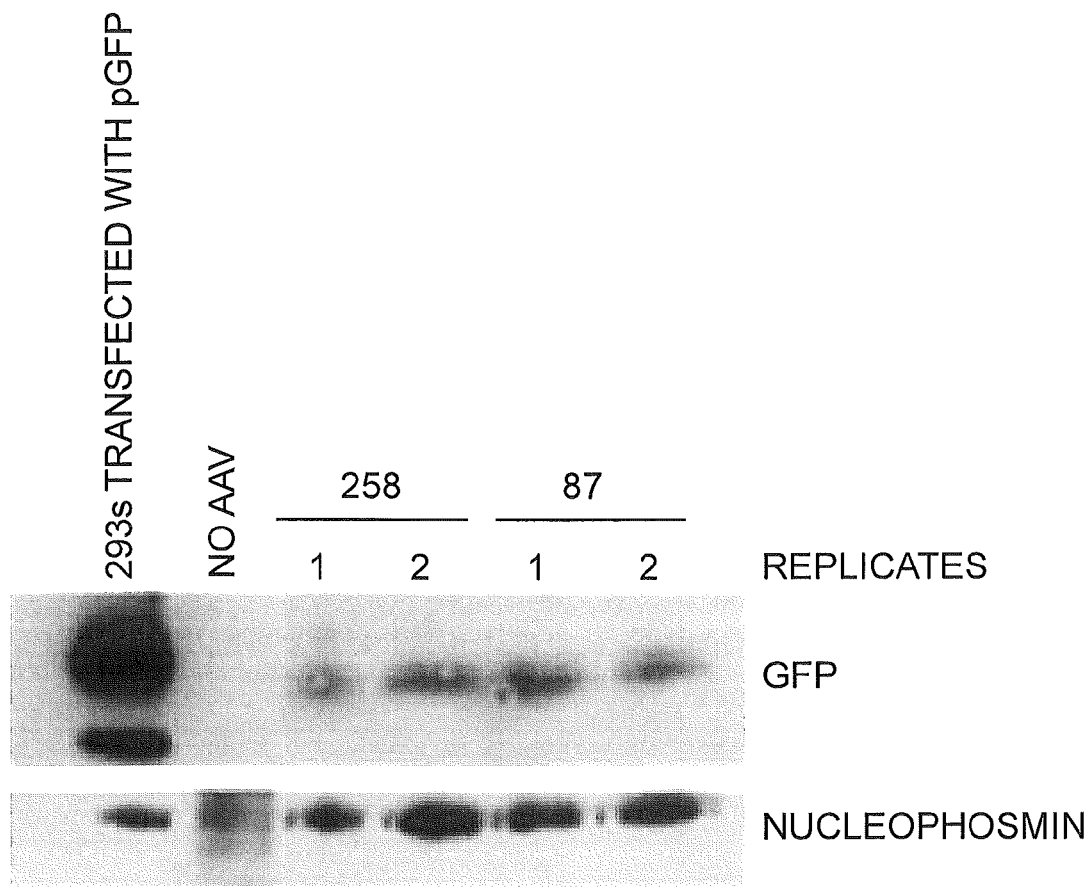
FIG. 9 shows synthetic ITR vector transduction in vivo. AAV2-CMV-eGFP vectors ($1 \times 10^8$ viral genomes) containing the WT ITR2 (87) or ITR-258 sequence were administered to the eye by intravitreal injection. Two weeks later, injected eyes were harvested and GFP abundance was evaluated by Western blot. Nucleophosmin was used as a loading control.

In vivo transduction ability was further tested in a different organ. AAV2-CMV-eGFP vectors ($1 \times 10^8$ viral genomes) containing the WT ITR2 (87) or ITR-258 sequence were administered to the eye by intravitreal injection. Two weeks later, injected eyes were harvested and GFP abundance was evaluated by Western blot (FIG. 9). Nucleophosmin was used as a loading control. The results show that ITR-258 was comparable to AAV ITR2 in GFP expression.

Example 4

Synthetic ITRs Alter Cellular Pathways

Figure 10:
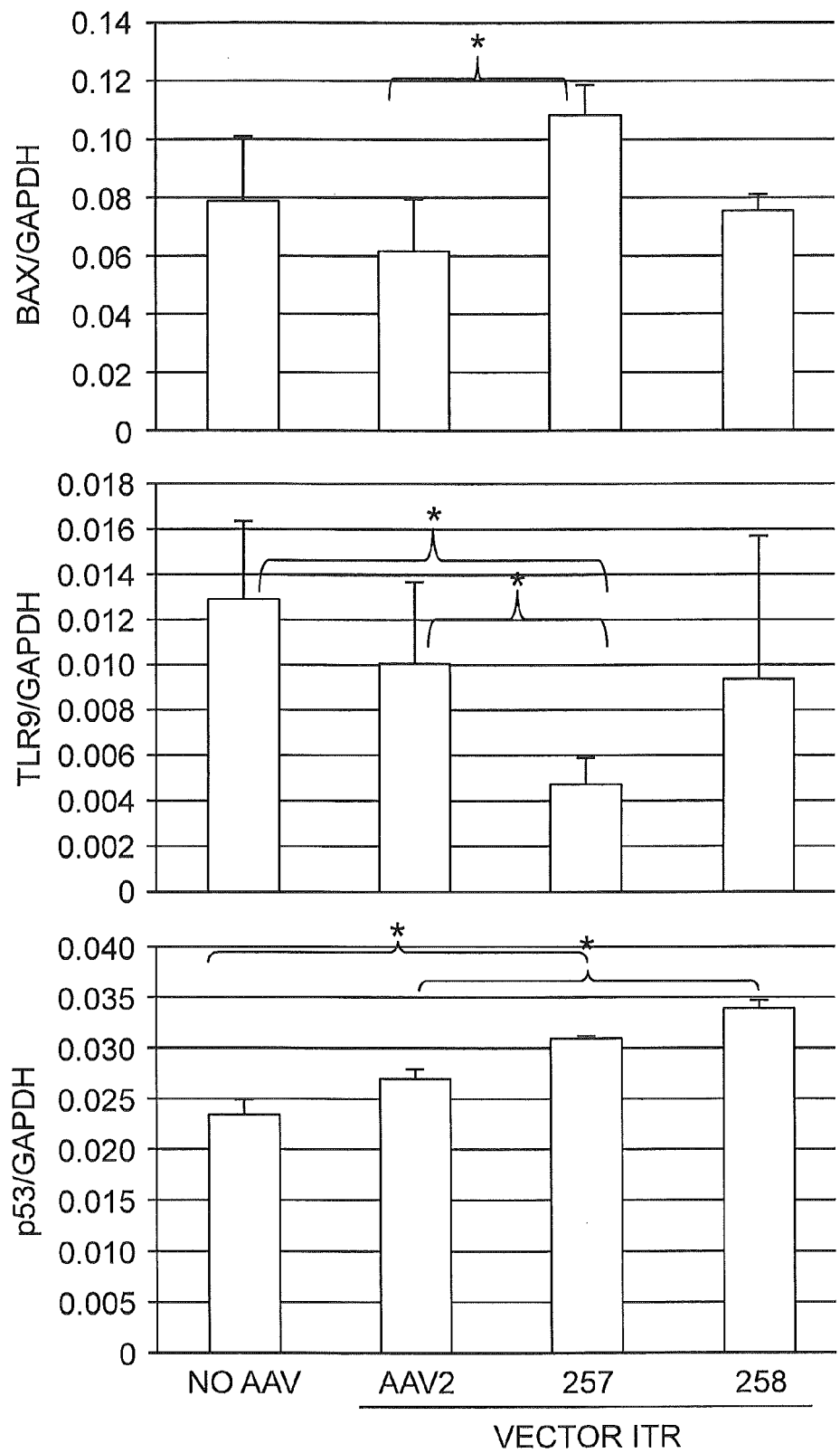
FIG. 10 shows the host's transcriptional response to synthetic inverted terminal repeat (ITR) vector transduction. Human fibroblasts were given the indicated vector and RNA was harvested 8 h later. Q-PCR was performed on cDNA using the indicated primer sets.

As the synthetic ITR vectors are deleted for putative transcription factor binding sites and altered in their CpG motif content, we investigated whether or not the host cell's transcriptional response in important regulatory cascades was altered upon transduction. These experiments were performed in a diploid human fibroblast line immortalized by h-TERT which displays normal a karyotype, an intact DNA damage response and cell cycle arrests. AAV CMV-eGFP vectors containing ITR-257 and ITR-258 were administered to cells at a viral genome to cell ratio of 10,000 in the AAV serotype 2 capsid. Eight hours post-infection RNA was isolated from treated cells using a kit (Qiagen) and used as template in cDNA synthesis reactions using reverse transcriptase. Q-PCR using the generated cDNA as the template was performed using toll like receptor 9 (TLR-9), Bax, and p53 primer sets and fluorescent probes specific to each primer set (Roche) (FIG. 10). The results, which are normalized to GAPDH cDNA, demonstrate that transduction by vectors containing the synthetic ITRs results in altered host responses at the levels of viral DNA recognition (TLR-9), DNA damage, and apoptosis signaling pathways (FIG. 10).

Figure 11:
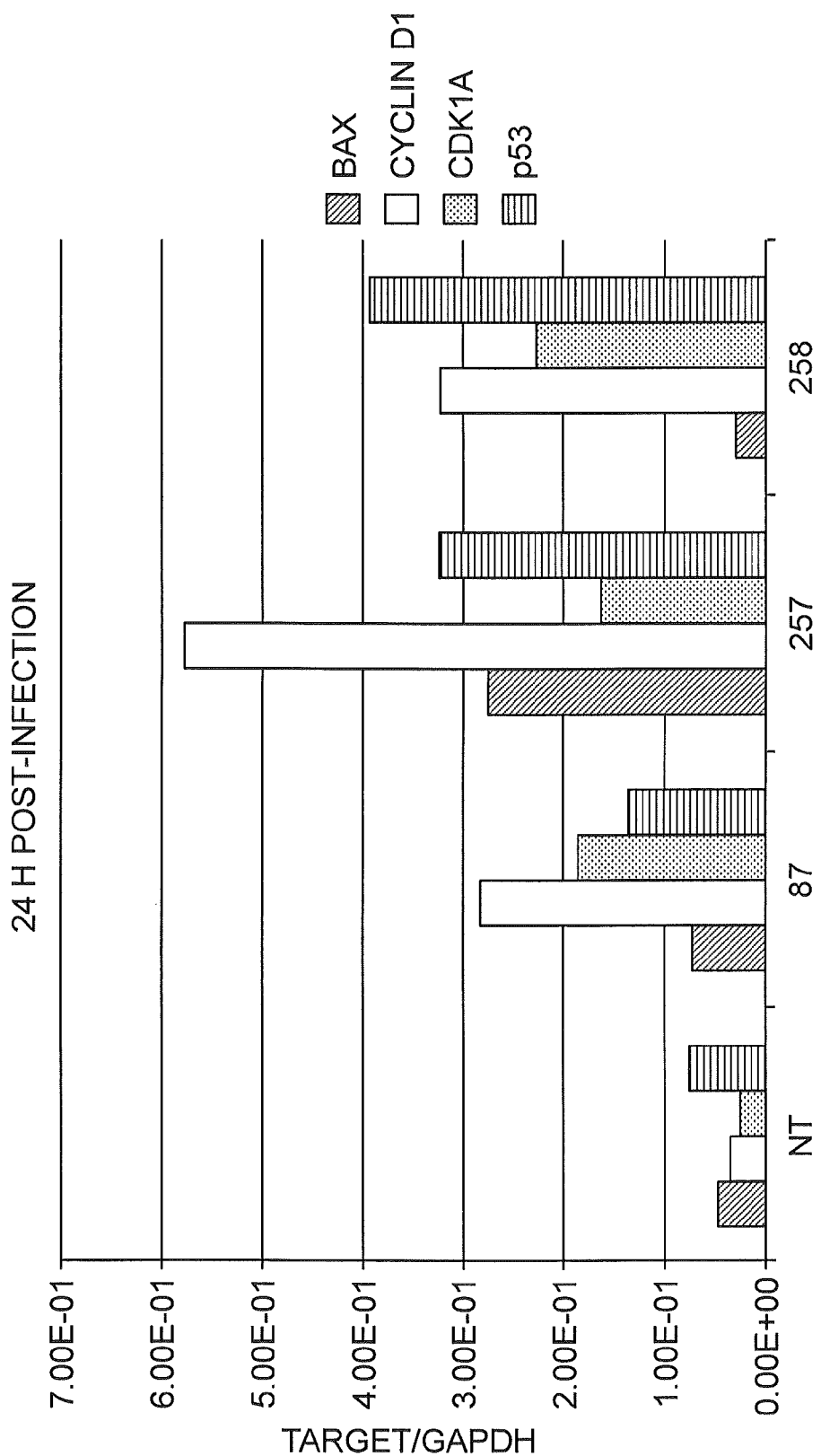
FIG. 11 shows the host's transcriptional response to synthetic inverted terminal repeat (ITR) vector transduction. Human fibroblasts were given the indicated vector and RNA was harvested 8 h later. Q-PCR was performed on cDNA using the indicated primer sets.

An additional study was done to measure expression of Bax, cyclin D1, cdk1A, and p53 (FIG. 11). Again the results demonstrate that transduction by vectors containing the synthetic ITRs result in an altered host responses, including cell cycle regulation.

Example 5

Promoter Activity of Synthetic ITRs

The WT ITR2 sequence has previously been shown to elicit promoter and enhancer functions [17, 18]. To determine if synthetic ITR-258 can also function as a promoter, the luciferase coding sequence and a polyA site was cloned approximately 60 nucleotides downstream of ITR-258 in the double-D vector context. AAV8-ITR258-luciferase vectors were produced and administered ($1 \times 10^{11}$ viral genomes) to a WT mouse via IV injection. Three weeks post-injection luciferase activity was evident in the liver using live imaging (IVIS) (FIG. 12). This result demonstrates that in the complete absence of a known promoter sequence, ITR-258 initiates transcription in vivo.

AAV vectors have been used for gene delivery in over 80 clinical trials for a variety of diseases [1]. In these cases, AAV gene delivery has been proven safe, and notable therapeutic outcomes include restoration of the Factor IX clotting factor in hemophilia B patients as well as restoring vision to those inflicted with Leber's congenital amaurosis [19-21]. Although the AAV capsid has been extensively modified towards increased transduction, little attention has been focused on alterations in the viral ITR, largely due to the difficulties in generating such a sequence. In this work, we have overcome these hurdles in ITR synthesis and generated the first wave of synthetic ITRs that allow vector production, infectivity and persistent transduction in vitro and in vivo. After defining the minimal synthetic sequence necessary for vector production we further analyzed 2 A-T rich ITRs that demonstrated unique transduction profiles (to each other and the AAV ITR2) upon infection (FIGS. 8 and 9). First, ITR-257 which contains 50% less CpG motifs and is substituted for putative ITR2 transcription factor binding sites demonstrated species dependent transduction biases (FIGS. 7-9). For instance, ITR-257 mediated similar levels as ITR2 in human cells but was approximately 3-fold decreased in mouse cells and in mouse skeletal muscle. In contrast, the smaller synthetic ITR-258 was enhanced for transduction, compared to AAV ITR2, in all contexts in vitro and in vivo (FIGS. 7-9).

At the level of the cellular response to AAV vector infection, we have noted differences in host signaling pathways attributable to the synthetic ITR sequence (FIGS. 10 and 11). Importantly, a cDNA analysis shortly after infection demonstrated the each of the synthetic ITRs has unique roles within the host compared to the natural ITR2 isolate. Our results demonstrate that anti-viral signaling (TLR-9), the DNA damage response (p53) and apoptosis are affected to varying degrees post-infection by the synthetic ITRs [22]. This observation serves as "proof of principle" of the ability to rationally design synthetic ITRs that exploit/avoid particular cellular signaling sequelae resulting in safer and enhanced AAV vectors.

Previous work has demonstrated that the AAV ITR2 contains promoter and promoter enhancer functions [17, 18]. Therefore, we investigated the ability of synthetic ITR-258 to initiate transcription in the absence of a known promoter sequence. The results of our in vivo analysis following IV vector administration demonstrates that, indeed, the ITR-258 initiates transcription and results in significant transgene activity (FIG. 12). Given that the ITR-258 is smaller than AAV ITR2 and has the ability to initiate transcription in vivo without a promoter, this synthetic ITR may be ideal for larger promoter-transgene cassettes beyond the 5 kb vector packaging limitation such as what is required for the treatment of multiple forms of muscular dystrophy, cystic fibrosis, Stargardts syndrome and hemophilia A.

WORKS CITED

1. Mitchell, A. M., et al., *AAV's anatomy: roadmap for optimizing vectors for translational success*. Curr Gene Ther, 2010. 10(5): p. 319-40.
2. Asokan, A., D. V. Schaffer, and R. J. Samulski, *The AAV Vector Toolkit: Poised at the Clinical Crossroads*. Mol Ther, 2012.
3. Samulski, R. J., et al., *Cloning of adeno-associated virus into pBR322: rescue of intact virus from the recombinant plasmid in human cells*. Proc Natl Acad Sci USA, 1982. 79(6): p. 2077-81.
4. Samulski, R. J., et al., *Rescue of adeno-associated virus from recombinant plasmids: gene correction within the terminal repeats of AAV*. Cell, 1983. 33(1): p. 135-43.
5. Hewitt, F. C. and R. J. Samulski, *Creating a novel origin of replication through modulating DNA-protein interfaces*. PLoS One, 2010. 5(1): p. e8850.

6. McCarty, D. M., P. E. Monahan, and R. J. Samulski, *Self-complementary recombinant adeno-associated virus (scAAV) vectors promote efficient transduction independently of DNA synthesis.* Gene Ther, 2001. 8(16): p. 1248-54.
7. Xiao, X., et al., *A novel 165-base-pair terminal repeat sequence is the sole cis requirement for the adeno-associated virus life cycle.* J Virol, 1997. 71(2): p. 941-8.
8. Zhong, L., et al., *Single polarity recombinant adeno-associated virus 2 vector-mediated transgene expression in vitro and in vivo: mechanism of transduction.* Mol Ther, 2008. 16(2): p. 290-5.
9. Ghosh, A., et al., *A hybrid vector system expands adeno-associated viral vector packaging capacity in a transgene-independent manner.* Mol Ther, 2008. 16(1): p. 124-30.
10. Grimm, D., et al., *Liver transduction with recombinant adeno-associated virus is primarily restricted by capsid serotype not vector genotype.* J Virol, 2006. 80(1): p. 426-39.
11. Snyder, R. O., et al., *Features of the adeno-associated virus origin involved in substrate recognition by the viral Rep protein.* J Virol, 1993. 67(10): p. 6096-104.
12. Ryan, J. H., S. Zolotukhin, and N. Muzyczka, *Sequence requirements for binding of Rep68 to the adeno-associated virus terminal repeats.* J Virol, 1996. 70(3): p. 1542-53.
13. McCarty, D. M., et al., *Identification of linear DNA sequences that specifically bind the adeno-associated virus Rep protein.* J Virol, 1994. 68(8): p. 4988-97.
14. McCarty, D. M., et al., *Interaction of the adeno-associated virus Rep protein with a sequence within the A palindrome of the viral terminal repeat.* J Virol, 1994. 68(8): p. 4998-5006.
15. Brister, J. R. and N. Muzyczka, *Rep-mediated nicking of the adeno-associated virus origin requires two biochemical activities, DNA helicase activity and transesterification.* J Virol, 1999. 73(11): p. 9325-36.
16. Brister, J. R. and N. Muzyczka, *Mechanism of Rep-mediated adeno-associated virus origin nicking.* J Virol, 2000. 74(17): p. 7762-71.
17. Li, C., et al., *A small regulatory element from chromosome 19 enhances liver-specific gene expression.* Gene Ther, 2009. 16(1): p. 43-51.
18. Haberman, R. P., T. J. McCown, and R. J. Samulski, *Novel transcriptional regulatory signals in the adeno-associated virus terminal repeat A/D junction element.* J Virol, 2000. 74(18): p. 8732-9.
19. Bennett, J., et al., *AAV2 gene therapy readministration in three adults with congenital blindness.* Sci Transl Med, 2012. 4(120): p. 120ra15.
20. Buchlis, G., et al., *Factor IX expression in skeletal muscle of a severe hemophilia B patient 10 years after AAV-mediated gene transfer.* Blood, 2012. 119(13): p. 3038-41.
21. High, K. A., *The gene therapy journey for hemophilia: are we there yet?* Blood, 2012. 120(23): p. 4482-7.
22. Hirsch, M. L., et al., *Viral single-strand DNA induces p53-dependent apoptosis in human embryonic stem cells.* PLoS One, 2011. 6(11): p. e27520.

The foregoing is illustrative of the present invention, and is not to be construed as limiting thereof. The invention is defined by the following claims, with equivalents of the claims to be included therein.

---

That which is claimed is:

1. A polynucleotide comprising at least one synthetic adeno-associated virus (AAV) inverted terminal repeat (ITR), wherein said ITR comprises:
   (a) an AAV rep binding element;
   (b) an AAV terminal resolution sequence; and
   (c) an AAV rep binding element' (RBE');
   wherein said ITR does not comprise any other AAV ITR sequences of 6 or more contiguous nucleotides.

2. The polynucleotide of claim 1, wherein (a), (b), and (c) are from AAV2 and said ITR does not comprise any other AAV2 ITR sequences.

3. The polynucleotide of claim 1, wherein said ITR further comprises non-AAV cis elements.

4. The polynucleotide of claim 1, wherein the nucleotide sequence of one or more transcription factor binding sites in said ITR is deleted and/or substituted.

5. The polynucleotide of claim 1, wherein said ITR is enhanced for intra- or inter-molecular homologous recombination compared to a naturally occurring AAV ITR.

6. The polynucleotide of claim 1, wherein said ITR exhibits increased host chromosome integration of transduced vector genomes compared to a naturally occurring AAV ITR.

7. The polynucleotide of claim 1, wherein said ITR exhibits decreased host chromosome integration of transduced vector genomes compared to a naturally occurring AAV ITR.

8. The polynucleotide of claim 1, wherein one or more CpG motifs in said ITR are deleted and/or substituted.

9. The polynucleotide of claim 1, further comprising a heterologous nucleic acid.

10. A viral vector comprising the polynucleotide of claim 1.

11. The viral vector of claim 10, which is an AAV vector.

12. A recombinant AAV particle comprising the polynucleotide of claim 1.

13. A method of producing a recombinant AAV particle, comprising providing to a cell permissive for AAV replication:

(a) a recombinant AAV template comprising (i) a heterologous nucleic acid, and (ii) the synthetic ITR of claim 1;
(b) a polynucleotide comprising Rep coding sequences and Cap coding sequences;
under conditions sufficient for the replication and packaging of the recombinant AAV template;
whereby recombinant AAV particles are produced in the cell.

14. The method of claim 13, wherein the Rep coding sequences and Cap coding sequences cannot be packaged into the recombinant AAV particles.

15. A method of delivering a nucleic acid to a cell, comprising introducing into a cell the recombinant AAV particle of claim 12.

16. The method of claim 15, wherein the cell is selected from the group consisting of a neural cell, lung cell, retinal cell, epithelial cell, smooth muscle cell, skeletal muscle cell, cardiac muscle cell, pancreatic cell, hepatic cell, kidney cell, myocardial cell, bone cell, spleen cell, keratinocyte, fibroblast, endothelial cell, prostate cell, germ cell, progenitor cell, stem cell, cancer cell, and tumor cell.

17. A method of administering a nucleic acid to a mammalian subject comprising administering to the mammalian subject a cell that has been contacted with the recombinant AAV particle of claim 12 under conditions sufficient for the AAV particle vector genome to enter the cell.

18. A method of administering a nucleic acid to a mammalian subject comprising administering to the mammalian subject the recombinant AAV particle of claim 12.

* * * * *

UNITED STATES PATENT AND TRADEMARK OFFICE
CERTIFICATE OF CORRECTION

PATENT NO. : 9,447,433 B2  
APPLICATION NO. : 14/211927  
DATED : September 20, 2016  
INVENTOR(S) : Hirsch et al.

Page 1 of 1

It is certified that error appears in the above-identified patent and that said Letters Patent is hereby corrected as shown below:

In the Specification

Column 31, Line 65: Please correct "β-sarcoglycan," to read -- δ-sarcoglycan, --

Signed and Sealed this  
Thirtieth Day of May, 2017

Michelle K. Lee  
*Director of the United States Patent and Trademark Office*